US011609224B2

(12) United States Patent
Chou et al.

(10) Patent No.: US 11,609,224 B2
(45) Date of Patent: Mar. 21, 2023

(54) DEVICES AND METHODS FOR WHITE BLOOD CELL ANALYSES

(71) Applicant: Essenlix Corporation, Monmouth Junction, NJ (US)

(72) Inventors: Stephen Y. Chou, Princeton, NJ (US); Wei Ding, East Windsor, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 742 days.

(21) Appl. No.: 16/172,710

(22) Filed: Oct. 26, 2018

(65) Prior Publication Data

US 2019/0128869 A1   May 2, 2019

Related U.S. Application Data

(60) Provisional application No. 62/577,353, filed on Oct. 26, 2017.

(51) Int. Cl.
*G01N 33/49* (2006.01)
*B01L 3/00* (2006.01)
(Continued)

(52) U.S. Cl.
CPC .......... *G01N 33/49* (2013.01); *B01L 3/5055* (2013.01); *B01L 3/502761* (2013.01); *G01N 15/0227* (2013.01); *G01N 15/14* (2013.01); *G01N 15/1431* (2013.01); *G01N 15/1434* (2013.01); *G01N 21/6428* (2013.01); *B01L 2200/021* (2013.01); *B01L 2200/0647* (2013.01); *B01L 2200/16* (2013.01); *B01L 2300/0816* (2013.01); *B01L 2300/0887* (2013.01); *B01L 2300/163* (2013.01); *B01L 2400/086* (2013.01); *G01N 2015/008* (2013.01); *G01N 2015/0073* (2013.01); *G01N 2015/0084* (2013.01); *G01N 2015/1006* (2013.01); *G01N 2015/1486* (2013.01); *G01N 2015/1493* (2013.01); *G01N 2015/1497* (2013.01); *G01N 2021/6439* (2013.01)

(58) Field of Classification Search
None
See application file for complete search history.

(56) References Cited

U.S. PATENT DOCUMENTS 3,368,872 A   2/1968   Natelson
3,447,863 A   6/1969   Patterson
(Continued)

FOREIGN PATENT DOCUMENTS

AU   198813789 A   9/1988
AU   619459 B   1/1992
(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015.
(Continued)

*Primary Examiner* — Xiaoyun R Xu

(57) ABSTRACT

Among other things, the present invention is related to devices and methods of performing biological and chemical assays, such as but not limited to assay related to analysis of white blood cells.

33 Claims, 4 Drawing Sheets

(51) Int. Cl.
    *G01N 21/64*    (2006.01)
    *G01N 15/14*    (2006.01)
    *G01N 15/02*    (2006.01)
    *G01N 15/00*    (2006.01)
    *G01N 15/10*    (2006.01)

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,083,761 A | 7/2000 | Kedar et al. |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,538,922 B2 * | 5/2009 | Pan .................... G02B 26/0833 359/290 |
| 7,547,424 B2 | 6/2009 | Haab et al. |
| 7,731,901 B2 | 6/2010 | Wardlaw |
| 7,738,094 B2 | 6/2010 | Goldberg |
| 7,799,558 B1 | 9/2010 | Dultz |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,144,504 B2 | 3/2012 | Kim et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,005,901 B2 | 4/2015 | Gayda et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |

(56) References Cited

U.S. PATENT DOCUMENTS

| | | |
|---|---|---|
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0180685 A1 | 7/2008 | de Lega et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2013/0316363 A1 | 11/2013 | Wainwright et al. |
| 2014/0170757 A1* | 6/2014 | Tsai .............. G01N 21/78 436/55 |
| 2014/0273076 A1 | 9/2014 | Adams et al. |
| 2014/0315242 A1 | 10/2014 | Rodriguez et al. |
| 2014/0323330 A1 | 10/2014 | Bergo |
| 2014/0368631 A1 | 12/2014 | Wardlaw et al. |
| 2015/0036131 A1 | 2/2015 | Salsman |
| 2015/0168302 A1* | 6/2015 | Dubach .............. G01N 21/6486 422/534 |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0004057 A1 | 1/2016 | Lin et al. |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2016/0350914 A1 | 12/2016 | Champlin et al. |
| 2016/0356999 A1 | 12/2016 | Fine |
| 2017/0021356 A1 | 1/2017 | Dority et al. |
| 2017/0038401 A1 | 2/2017 | Holmes et al. |
| 2017/0045504 A1 | 2/2017 | Bloom |
| 2017/0189906 A1 | 7/2017 | Moll et al. |
| 2017/0293133 A1 | 10/2017 | Fine |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 2848196 | 3/2015 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017027643 | 2/2017 |
| WO | 2017048871 | 3/2017 |
| WO | 2017048881 | 3/2017 |

OTHER PUBLICATIONS

Jahanmehr, S A H et al., Simple technique for fluorescence staining of blood cells with acridine orange, Technical Methods, Feb. 12, 1987.

Sun, Wei et al., Rapid antimicrobial susceptibility test for identification of new therapeutics and drug combinations against multidrug-resistant bacteria, Emerg. Microbes Infect., Nov. 9, 2016.

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.

Written Opinion for PCT/US2018/017713 established by ISA/KR, dated Jun. 20, 2018.

* cited by examiner

DEVICES AND METHODS FOR WHITE
BLOOD CELL ANALYSES

FIELD

Among other things, the present invention is related to devices and methods of performing biological and chemical assays, such as but not limited to assay related to analysis of white blood cells.

BACKGROUND

In biological and chemical assays (e.g. diagnostic testing), it is often necessary to measure and/or detect analytes of a sample or a part of the sample, quickly and simply. The current invention provides devices and methods for achieving these goals.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Examples of QMAX Device with Hinges (QMAX Card)

Figure 1:
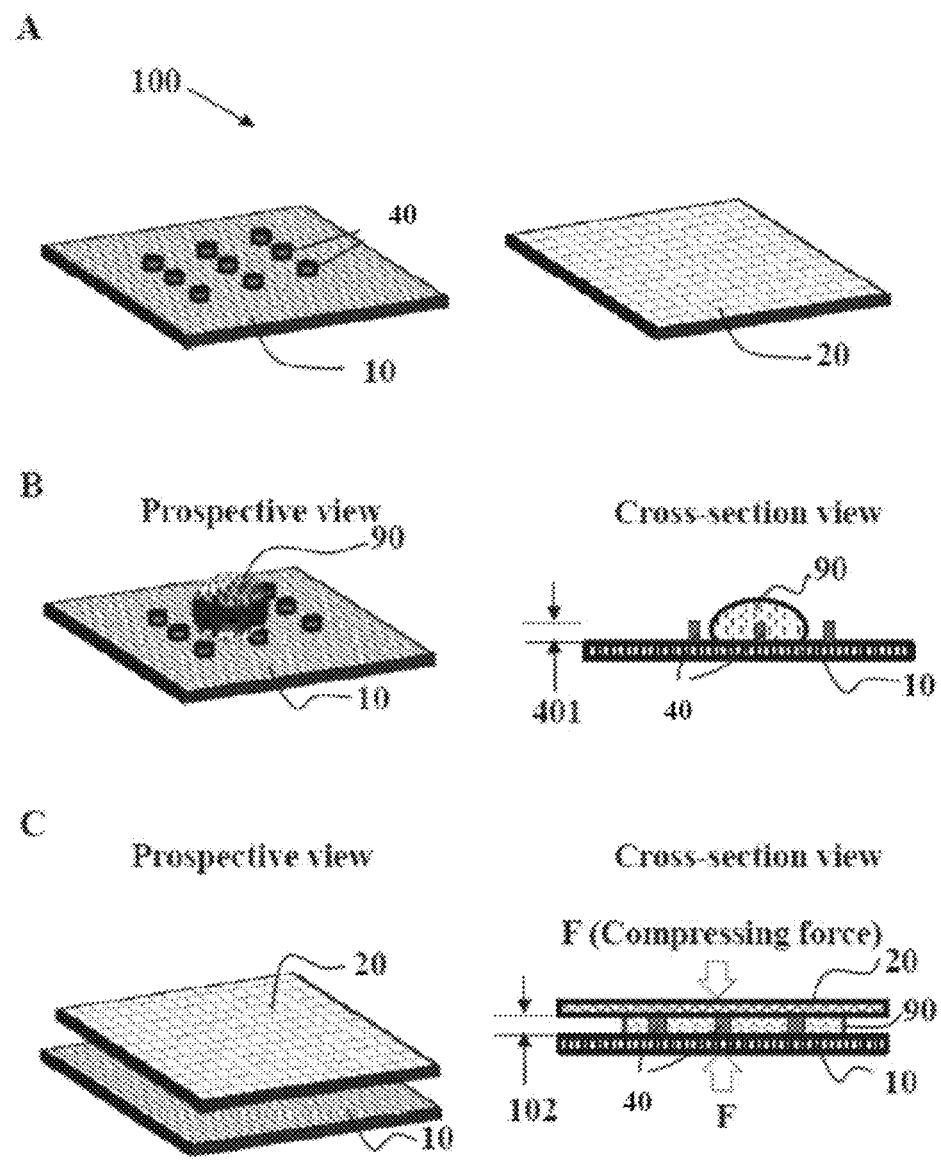
FIG. 1 shows an embodiment of a QMAX (Q: quantification; M: magnifying; A: adding reagents; X: acceleration; also known as compressed regulated open flow (CROF)) device, which comprises a first plate and a second plate. Panel (A) shows the perspective view of the plates in an open configuration when the plates are separated apart; panel (B) shows the perspective view and a sectional view of depositing a sample on the first plate at the open configuration; panel (C) the perspective view and a sectional view of the QMAX device in a closed configuration.

FIG. 1 shows an embodiment of a generic QMAX (Q: quantification; M: magnifying; A: adding reagents; X: acceleration; also known as compressed regulated open flow (CROF)) device. The generic QMAX device comprises a first plate 10 and a second plate 2. In particular, panel (A) shows the perspective view of a first plate 10 and a second plate 20 wherein the first plate has spacers. It should be noted, however, that the spacers can also be fixed on the second plate 20 (not shown) or on both first plate 10 and second plate 20 (not shown). Panel (B) shows the perspective view and a sectional view of depositing a sample 90 on the first plate 10 at an open configuration. It should be noted, however, that the sample 90 also can also be deposited on the second plate 20 (not shown), or on both the first plate 10 and the second plate 20 (not shown). Panel (C) illustrates (i) using the first plate 10 and second plate 20 to spread the sample 90 (the sample flow between the inner surfaces of the plates) and reduce the sample thickness, and (ii) using the spacers and the plate to regulate the sample thickness at the closed configuration of the QMAX device. The inner surfaces of each plate have one or a plurality of binding sites and or storage sites (not shown).

In some embodiments, the spacers 40 have a predetermined uniform height and a predetermined uniform interspacer distance. In the closed configuration, as shown in panel (C) of FIG. 1, the spacing between the plates and the thus the thickness of the sample 90 is regulated by the spacers 40. In some embodiments, the uniform thickness of the sample 90 is substantially similar to the uniform height of the spacers 40. It should be noted that although FIG. 1 shows the spacers 40 to be fixed on one of the plates, in some embodiments the spacers are not fixed. For example, in certain embodiments the spacers are mixed with the sample so that when the sample is compressed into a thin layer, the spacers, which is rigid beads or particles that have a uniform size, regulate the thickness of the sample layer.

QMAX Assay

In biological and chemical assaying (i.e. testing), a device and/or a method that simplifies assaying operation or accelerates assaying speed is often of great value.

In the QMAX (Q: quantification; M: magnifying; A: adding reagents; X: acceleration; also known as compressed regulated open flow (CROF)) assay platform, a QMAX card uses two plates to manipulate the shape of a sample into a thin layer (e.g. by compressing) (as illustrated in FIG. 1). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connects the two or more plates, so that the plates can open and close in a similar fashion as a book.

In certain embodiments, the hinge is configured so that the hinge can self-maintain the angle between the plates after adjustment.

In certain embodiments, the hinge is configured so that the material of the hinge, which maintain the QMAX card in the closed configuration, such that the entire QMAX card can be slide in and slide out a card slot without causing accidental separation of the two plates.

Another aspect of the present invention is to provide opening mechanisms such as but not limited to notches on plate edges or strips attached to the plates, making is easier for a user to manipulate the positioning of the plates, such as but not limited to separating the plates of by hand.

Another aspect of the present invention is to provide a hinge that can control the rotation of more than two plates.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX device.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX device refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX device refers the device that perform a QMAX (e.g. CROF) process on a sample, and have or not have a hinge that connect the two plates.

The term "QMAX device with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

QMAX Device and Assay for Cell Counting

The QMAX device can be used to analyze fluid samples, such as but not limited to biological fluid samples. In some embodiments, the QMAX device is used to analyze a blood sample. For example, in certain embodiments, the QMAX device is used to measure the amount of certain analytes, e.g. counting of red blood cells (RBC), white blood cells (WBC), and/or subtypes of certain blood cells. In certain embodiments, the QMAX device can be used for the counting of WBC. In certain embodiments, staining reagents can be used to label the cells and structures, such as but not be limited to RBC, WBC (including WBC subtypes), and platelets.

As shown in FIG. 1, various parameters of the QMAX device can vary based on specific tests. For example, in some embodiment, the spacer height is less than 0.2 um, 0.5 um, 0.8 um, 1 um, 1.2 um, 1.5 um, 1.8 um, 2 um, 3 um, 4 um, 5 um, 6 um, 7 um, 8 um, 9 um, 10 um, 11 um, 12 um, 13 um, 14 um, 15 um, 16 um, 17 um, 18 um, 19 um, 20 um, 25 um, 30 um, 35 um, 40 um, 45 um, 50 um, 60 um, 70 um, 75 um, 80 um, 90 um, 100 um, 125 um, 150 um, 175 um, 200 um, 250 um, 300 um, 350 um, 400 um, 450 um, 500 um, 600 um, 700 um, 800 um, 900 um, 1 mm, 2 mm, 3 mm, 4 mm, 5 mm, 10 mm, or in a range between any of the two values. In the closed configuration, the uniform thickness of the sample layer is substantially the same as the gap between the QMAX plates, which is substantially the same as the spacer height. Therefore, the descriptions to the spacer height also apply to the thickness of the sample layer and the QMAX gap, and vice versa.

In some embodiments of the QMAX assay, the sample is deposited to one or both of the plates in the open configuration; then the plates are pressed into a closed configuration so that at least part of the sample compressed into a layer of highly uniform thickness, which is stagnant to the plates and confined by the inner surfaces of the plates. In some embodiments, an analyte in the sample is measured. In certain embodiments, the analyte is a type of cells that can be counted. For example, in certain embodiments the sample is a blood sample and the analyte is red blood cells; in certain embodiments the sample is a blood sample and the analyte is white blood cells; in certain embodiments the sample is a blood sample and the analyte is white blood cell sub-types (including neutrophils, eosinophils, basophils, lymphocytes, and monocytes).

In some embodiments, when the QMAX device is in the closed configuration, a camera can be used to capture images of the sample layer. In certain embodiments, the camera can have a field of view (FoV), which is defined as the area of sample of which the image can be captured by the camera. In certain embodiments, the camera is part of a device, such as but not limited to a mobile device. In certain embodiments, the mobile device is a smart phone, a tablet computer, or a laptop computer. In some embodiments, the mobile device is a mobile communication device such as a smart phone. In certain embodiments, the camera has one lens; in certain embodiments, the camera has two lenses that are aligned parallel to each other.

In some embodiments, different spacer height (hence different sample thickness and QMAX gap) can affect the accuracy of the counting of certain cells, such as but not limited to white blood cells and sub-types of white blood cells. For example, for counting white blood cells (WBC), spacer height and FoV can affect the accuracy and consistency of the counting results. With an acceptable level of consistency, the direct counting results can be adjusted to reflect the real number of cells, providing basis for diagnostics and health guidance. In certain embodiments, one factor that needs to be considered is the consistency of "miss count" rate, which is the deviation of the results with a method being tested from the real number, which is usually established with a well-defined and well-accepted method. It should also be noted that the method herein disclosed can be applied to not only WBC counting, but also other assays.

The device and method of the current invention can be used to (1) count the white blood cells, (b) count the white blood cells sub-types (including neutrophils, eosinophils, basophils, lymphocytes, and monocytes), and (3) differentiate white blood cells, wherein the device further comprises spacers that regulate the spacing between the sample contact areas when the plates are in a closed configuration.

In some embodiments, the average thickness of the layer of uniform thickness is in the range of 5.0 um to 8.5 um.

In some embodiments, the average thickness of the layer of uniform thickness is in the range of 7.5 um to 10.5 um.

In some embodiments, the average thickness of the layer of uniform thickness is in the range of 9.5 um to 12.5 um.

In some embodiments, the average thickness of the layer of uniform thickness is in the range of 9.5 um to 12.5 um.

In some embodiments, the average thickness of the layer of uniform thickness is in the range of 11.5 um to 13.5 um.

In some embodiments, the average thickness of the layer of uniform thickness is in the range of 12.5 um to 14.5 um.

In some embodiments, the average thickness of the layer of uniform thickness is in the range of 13.5 um to 16 um.

In some embodiments, the spacer height is in the range of 5.0 um to 8.5 um.

In some embodiments, the spacer height is in the range of 7.5 um to 10.5 um.

In some embodiments, the spacer height is in the range of 9.5 um to 12.5 um.

In some embodiments, the spacer height is in the range of 9.5 um to 12.5 um.

In some embodiments, the spacer height is in the range of 11.5 um to 13.5 um.

In some embodiments, the spacer height is in the range of 12.5 um to 14.5 um.

In some embodiments, the spacer height is in the range of 13.5 um to 16 um.

In some embodiments, the field of view for counting and differentiating WBCs is 0.1 mm$^2$, 10 mm$^2$, 50 mm$^2$, 100 mm$^2$ or a range between any two of the values.

In some embodiments, when the gap size of the QMAX device is about 10 um, the FoV is larger than 36 mm$^2$, thereby the WBC counting and differentiation accuracy is less than 5%.

In some embodiments, when the gap size of device is 10 um, the FoV is larger than 16 mm$^2$, thereby the WBC counting and differentiation accuracy is less than 10%.

In some embodiments, when the gap size of device is 10 um, the FoV is larger than 2 mm$^2$, thereby the WBC counting and differentiation accuracy is less than 20%.

In some embodiments, the field of view is in the range of 0.1 mm$^2$ to 10 mm$^2$, the preferred gap size of device is in the range of 10 um to 30 um, 30 um to 50 um, thereby the counting and differentiation accuracy is less than 10%.

In some embodiments, the field of view is in the range of 0.1 mm$^2$ to 10 mm$^2$, the preferred gap size of device is in the range of 10 um to 30 um, thereby the counting and differentiation accuracy is less than 20%.

In some embodiments, the field of view is in the range of 10 mm$^2$ to 50 mm$^2$, the preferred gap size of device is in the range of 5 um to 10 um, 10 um to 30 um, thereby the counting and differentiation accuracy is less than 10%.

In some embodiments, the field of view is in the range of 10 mm$^2$ to 50 mm$^2$, the preferred gap size of device is in the range of 2 um to 5 um, 5 um to 10 um, 10 um to 30 um, thereby the counting and differentiation accuracy is less than 20%.

In some embodiments, the field of view is in the range of 50 mm$^2$ to 100 mm$^2$, preferred gap size of device is in the range of 2 um to 5 um, 5 um to 10 um, 10 um to 30 um, 30 um to 50 um thereby the counting and differentiation accuracy is less than 10%.

In some embodiments, the spacer has a height of preferred range of 2 um to 5 um, thereby the WBCs missing counting is less than 15%.

In some embodiments, the spacer has a height of preferred range of 2 um to 5 um, 5 um to 10 um, thereby the WBCs missing counting is less than 30%.

In some embodiments, the spacer has a height of preferred range of 2 um to 5 um, 5 um to 10 um, 10 um to 30 um thereby the WBCs missing counting is less than 60%.

In some embodiments, the sample to camera lens distance is in the range of 2 mm to 5 mm.

In some embodiments, the sample to camera lens distance is in the range of 4 mm to 7 mm.

In some embodiments, the sample to camera lens distance is in the range of 6 mm to 9 mm.

In some embodiments, the sample to camera lens distance is in the range of 8 mm to 11 mm.

In some embodiments, the sample to camera lens distance is in the range of 10 mm to 13 mm.

In some embodiments, the sample to camera lens distance is in the range of 12 mm to 15 mm.

Examples of QMAX Device for Counting White Blood Cells

Figure 2:
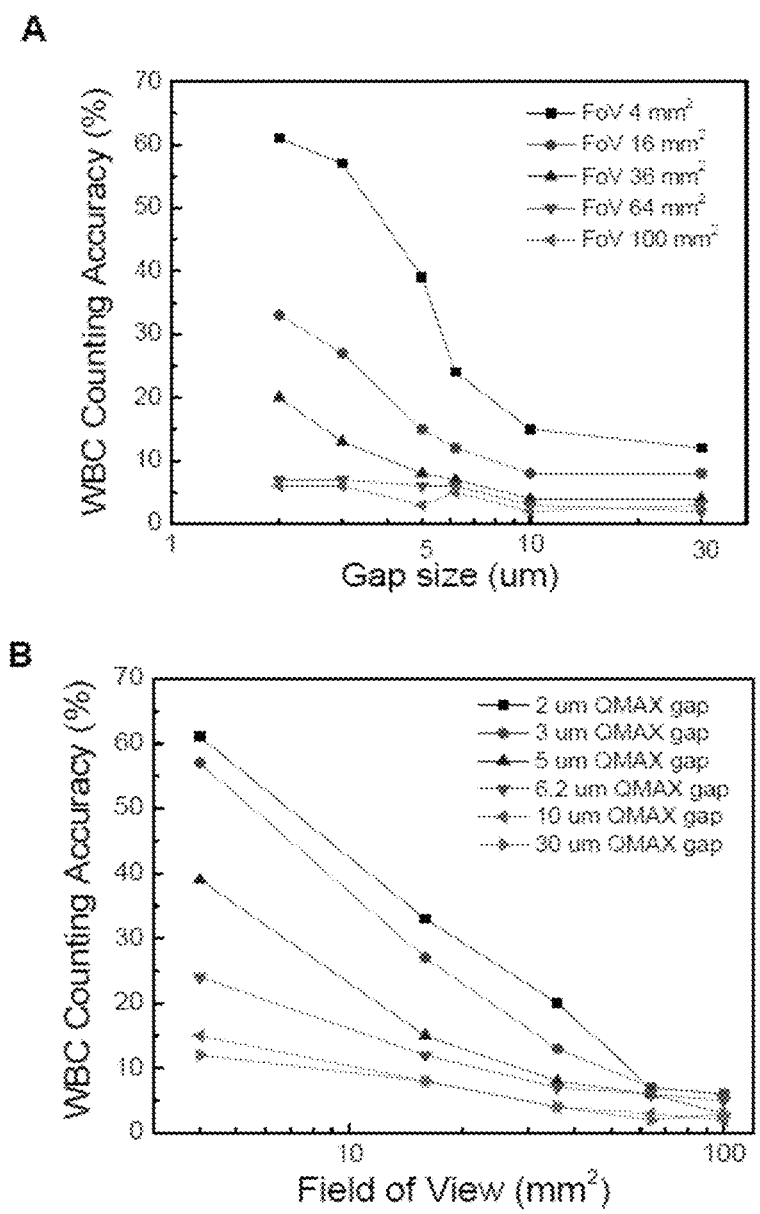
FIG. 2 illustrates white blood cell (WBC) counting accuracy vs. field of view (FoV) vs. QMAX gap (thickness of sample layer). Panel (A) shows plots of WBC counting accuracy vs. QMAX gap size with effective FoV of 4 mm$^2$, 16 mm$^2$, 36 mm$^2$, 64 mm$^2$, and 100 mm$^2$; panel (B) shows plots of WBC counting accuracy FoV with QMAX gap size of 2 um, 3 um, 5 um, 6.2 um, 10 um and 30 um.

FIG. 2 illustrates white blood cell (WBC) counting accuracy vs. field of view (FoV) vs. QMAX gap (thickness of sample layer). Undiluted blood was deposited on one or both of the plates of the QMAX device in the open configuration; the plates were pressed into a closed configuration so that at least part of the sample was compressed into a layer of uniform thickness; a camera in a smart phone was used to capture images of the compressed sample; the number of WBC was counted by analyzing the images.

Panel (A) of FIG. 2 shows plots of WBC counting accuracy vs. QMAX gap size with effective FoV of 4 mm$^2$, 16 mm$^2$, 36 mm$^2$, 64 mm$^2$, and 100 mm$^2$; panel (B) shows plots of WBC counting accuracy FoV with QMAX gap size of 2 um, 3 um, 5 um, 6.2 um, 10 um and 30 um. The results are also summarized in Table 1.

TABLE 1

WBC counting accuracy vs. Field of View vs. QMAX gap

| Field of View | QMAX gap size (um) | | | | | |
|---|---|---|---|---|---|---|
| (mm$^2$) | 2 | 3 | 5 | 6.2 | 10 | 30 |
| 4 | 61% | 57% | 39% | 24% | 15% | 12% |
| 16 | 33% | 27% | 15% | 12% | 8% | 8% |
| 36 | 20% | 13% | 8% | 7% | 4% | 4% |
| 64 | 7% | 7% | 6% | 6% | 3% | 2% |
| 100 | 6% | 6% | 3% | 5% | 2% | 3% |

In this set of experiments, the first plate of the QMAX device is 1 mm thick PMMA with printed acridine orange dye, and the second plate is X-Plate with spacers having 30×40 um pillar size, 80 um inter spacing distance, made on 175 um thick PMMA. 1 uL fresh blood without any anticoagulant was used in the test and deposited on the first plate. Counting accuracy is defined as the counting number's standard deviation for all the fields on card with a specific FoV. This counting accuracy represents the case when a field with FoV in the sample layer is randomly picked for measure, how accurate it represents the average number of all the fields. Generally, WBC counting is more accurate with larger field of view and larger QMAX gap. In essence, counting accuracy here reflects the consistency of the method with specific gap size and field of view.

Table 2 shows in certain case of using fluorescence measuring WBC, the relationship between WBC miss counting and correction factor vs. QMAX gap. Herein, miss counting rate is defined as the percentage difference between the back-calculated WBC concentration (from counting number, counting area, filling factor, gap size) and sample's real WBC concentrations (measured by calibrated commercial hematology machine).

Correction factor=1/(1−Missing Counting Rate).

TABLE 2

WBC miss counting & correction factor vs. QMAX gap

| QMAX gap size (um) | WBC miss counting | WBC correction factor |
|---|---|---|
| 2 | 0% | 1 |
| 3 | 0% | 1 |
| 5 | 10% | 1.1 |
| 10 | 25% | 1.3 |
| 30 | 50% | 2.0 |

As shown in Table 2, the miss counting rate increases with the gap size (thus spacer height and sample thickness). Furthermore, additional experiments show that differentiated WBC (Granulocytes, Lymphocyte, Monocyte) counting has similar miss counting rate with WBC total counting. In addition, WBC miss counting rate is not influenced by field of view.

As shown in FIG. 2, panels (A) and (B), the counting accuracy, which reflects the consistency of the counting at certain gap sizes and field of view, is higher with a larger gap size and a larger field of view, respectively. Therefore, in some embodiments, certain gap sizes (thus spacer heights) and/or field of view size can be chosen to obtain an acceptable level of consistency, and/or prevent high level of miss count.

With the correction factor, which is based on the miss counting rate, the counting result can be adjusted to provide a more accurate and consistent number for medical and health purposes. In some embodiments, the final number equals the counting results multiplies the correction factor.

Table 3 shows the calculation of self-overlap rate of WBC cell vs. QMAX gap. In general, more WBCs are overlapped when the gap size is larger, especially larger than 30 um.

TABLE 3

QMAX gap size vs. WBC distance vs. Overlap rate

| CROF gap (um) | Cell 2D Distance (um) | Overlap Rate |
|---|---|---|
| 2 | 320 | 0% |
| 10 | 140 | 0% |
| 30 | 80 | 1% |
| 50 | 60 | 2% |
| 70 | 50 | 5% |
| 100 | 45 | 9% |
| 300 | 25 | 66% |

Exemplary Embodiments with a Gap of 8 to 12 um

The experiments (see e.g. FIGS. 2-3) show that for the measurement of WBC in undiluted blood sample, with a given field of view provide by a camera (e.g. camera in a mobile phone), a spacer height of 5 to 15 um provides more accurate results than spacer height of 2 um to 3 um. In some embodiments, a QMAX device for WBC measurement has spacer height of 5 to 15 um. In certain embodiments, the QMAX device has a spacer height of 10 um, while a same of a similar sample thickness uniformity can be achieved. In some embodiments, such pillar heights have advantage for imaging and counting the white blood cells in an undiluted blood.

Exemplary Embodiments of Optical Adapter

In some embodiments, the QMAX device (e.g. in the form of a QMAX card) with sample can be inserted into an adaptor, which can be attached to a device that comprises a camera and/or an illumination source. In certain embodiments, the device is a mobile communication device, such as but not limited to a smart phone.

Figure 3:
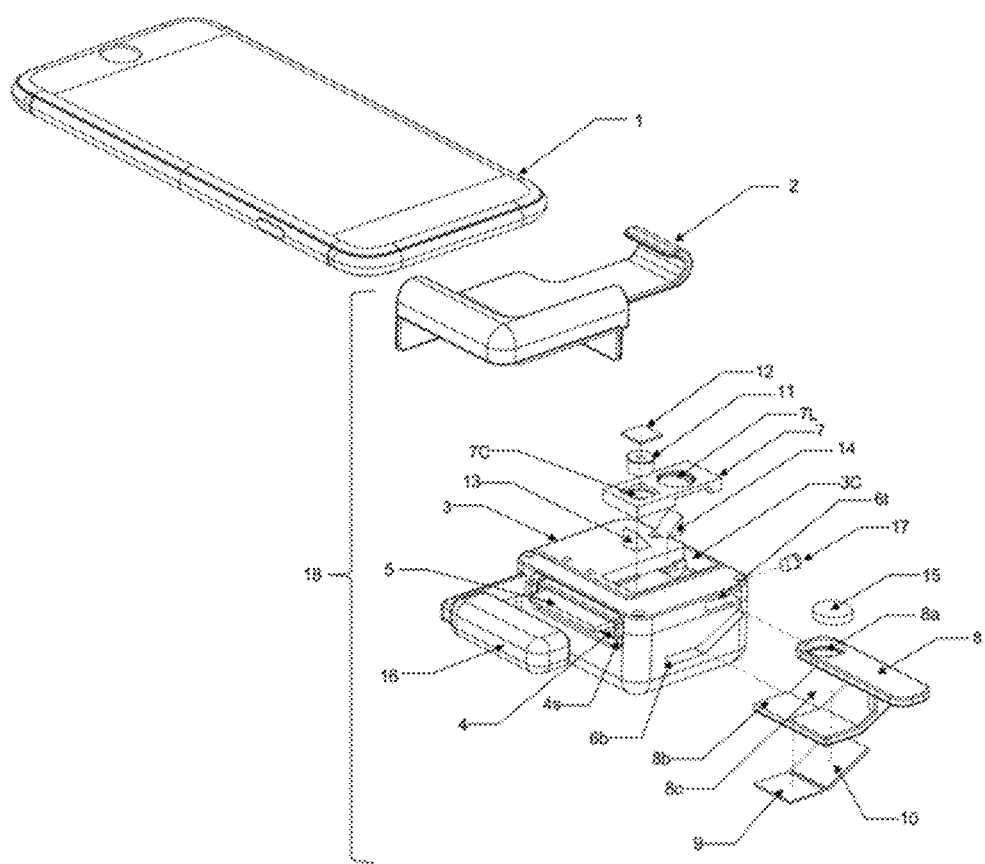
FIG. 3 shows a schematic exploded view of an optical adaptor device for attaching the QMAX device to a mobile communication device.

FIG. 3 shows a schematic exploded view of an optical adaptor device for attaching the QMAX device to a mobile communication device and for measurement of an analyte in the sample. Here the optical adaptor device 18 is in system 19, which comprises the mobile communication device (smart phone) 1.

Adaptor 18 comprises a holder case 2 fitting over the upper part of smartphone 1; an optical box 3 attached to case 2 including a receptacle slot 4, an optics chamber 3C, track 6b and 6t allowing lever 8 to slide in, and a rubber door 16 inserted into trench 4s to cover receptacle slot 4. An optics insert 7 is fitted into the top of optics chamber 3C with an exit aperture 7L and an entrance aperture 7C in it aligning with light source 1L and camera 1C (referring to FIG. 4) in smartphone 1. A lens 11 is mounted in entrance aperture 7C in optics insert 7 and configured so that the sample in sample slide 5 inserted into receptacle slot 4 is located within the working distance of the camera 1C (referring to FIG. 4). Lens 11 serves to magnify the images of the sample captured by camera 1C (referring to FIG. 4). A long-pass optical filter 12 is mounted on top of lens 11 in entrance aperture 7C. A pair of right-angle mirrors 13 and 14 are mounted on the bottom of optics chamber 3C and configured so that mirror 13 and mirror 14 are aligned with light source 1L and camera 1C (referring to FIG. 4) respectively. Mirror 13 and mirror 14 whose operation as bright-field illumination optics in device 18 is described below in FIG. 4.

Lever 8 comprises two level bars: the upper-level bar comprises a band-pass optical filter 15 mounted in slot 8a, and the lower-level bar comprises a light absorber 9 mounted on the horizontal plane 8b and a reflective mirror 10 mounted on the tilted plane 8c. The optical filter 15, light absorber 9 and mirror 10 whose operation as fluorescent illumination optics in device 18 is described in FIG. 4. The upper-level bar of lever 8 slides along track 6t in box 3 and lower-level bar 8b and 8c slides along track 6b in box 3. Lever 8 stops at two different positions in box 3 to switch between bright-field illumination optics and fluorescent illumination optics. Lever 8 is fully inserted into box 3 to switch device 18 to work with fluorescent illumination optics. Ball plunger 17 is mounted on the sidewall of track 6t to stop lever 8 at a pre-defined position when lever 8 being pulled outward from box 3 to switch device 18 to work with bright-field illumination optics.

Figure 4:
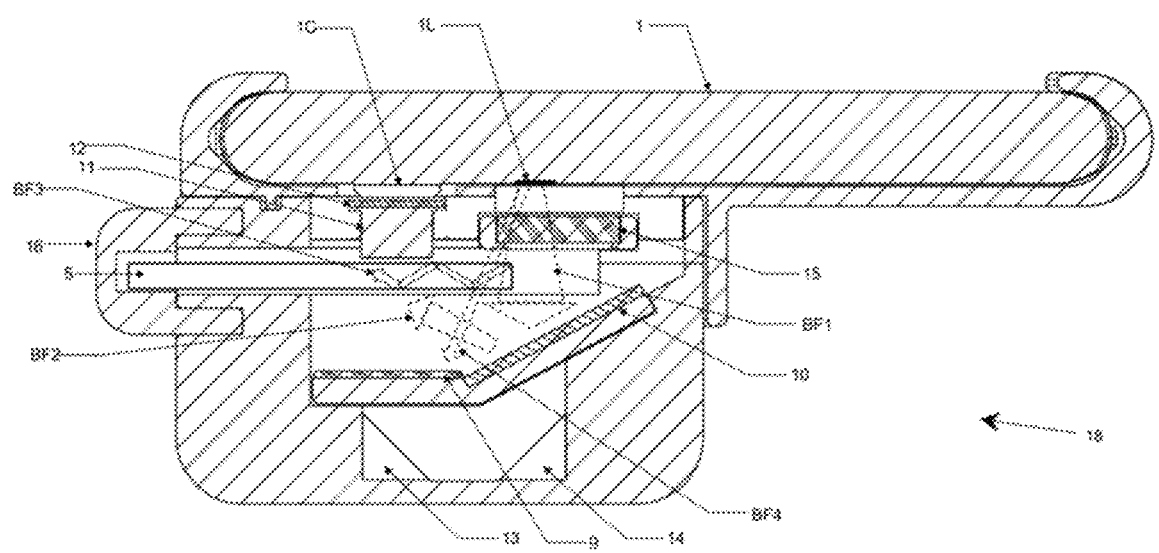
FIG. 4 shows a schematic sectional view with details of a system that can be used to test a sample in fluorescent illumination mode, and particularly of the optical adapter.

FIG. 4 shows a schematic sectional view with details of a system that can be used to test a sample in fluorescent illumination mode, and particularly of the optical adaptor. This FIG. 4 illustrates the functionality of the elements that were described above with reference to FIG. 3. Lever 8 (shown in FIG. 3) is fully inserted into device 18 so that light absorber 9 and tilted mirror 10 are under the view of camera 1C and light source 1L, and block the light path between light source 1L and the pair of mirrors of 13 and 14. And band-pass optical filter 15 is right under the light source 1L. Light source 1L emits light beam BF1 away from smartphone 1. Optical filter 15 allows beam BF1 with specific wavelength range which matches the excitation wavelength of the fluorescent sample in sample slide 5 to go through. Part of beam BF1 illuminates on the edge of transparent sample slide 5 and couples to waveguide beam BF3 travelling in sample slide 5 and illuminates the sample area under the lens 11. Part of beam BF1 illuminates on mirror 10. Tilted mirror 10 deflects beam BF1 to beam BF2 and back-illuminates the sample area in sample slide 5 right under lens 11 in large oblique angle. The remaining part of beam BF1 with large divergence angle (i.e., beam BF4) illuminates on absorber 9 and get absorbed so that no reflected light of beam BF4 gets into the camera 1C in small incidence angle. The light coming from the sample area under the lens 11 goes through the lens 11 and is filtered by long-pass filter 12 so that only light in a specify wavelength range that is emitted by the fluorescent sample in sample slide 5 gets into camera 1C to form an image. Smartphone 1 captures and processes the image to get some property of the sample. Rubber door 16 is inserted into device 18 to cover sample slide 5 to prevent ambient light getting into device 18 to affect the test.

In some embodiments, the adapter as described in FIGS. 3 and 4 can be used to measure a blood sample, e.g. undiluted whole blood sample. In certain embodiments, the analyte can be WBC, which requires the lever 8 to be inserted for optimal reading. In some embodiments, the adapter comprises:

(a) an attachment member configured to attach the adapter to an apparatus that comprises a light source and a camera;

(b) a card slot configured to accommodate a sample card, which contains a liquid sample that is compressed into a layer of uniform thickness, wherein when the sample card inserted into the card slot, the sample is positioned under the view of the camera and the light source;

(c) an optical filter configured to filter light from the light source to form a first beam with a specific wavelength range, wherein a part of the first beam illuminates on the edge of the sample card and travels in the sample card to illuminate the sample;

(d) a mirror configured to deflect part of the first beam to form a second beam that back-illuminates the sample in an oblique angle;

(e) an absorber configured to absorb a remaining part of the first beam that has a divergence angle.

In some embodiments, the method to measure an analyte, such as but not limited to WBC, in a liquid sample, can comprises:

(a) obtaining the liquid sample;

(b) compressing at least part of the sample into a layer of uniform thickness with a sample card, (c) inserting the sample card into an adaptor device, which is configured to be attached to an apparatus that comprises a light source and a camera;

(d) illuminating the sample with light from the light source, wherein i. the light is filtered by an optical filter of the adapter device to form a first beam with a specific wavelength range, part of the first beam illuminating on the edge of the sample card and travels in the sample card to illuminate the sample;

ii. part of the first beam is deflected by a mirror of the adapter device to form a second beam that back-illuminates the sample in an oblique angle; and iii. a remaining part of the first beam that has a divergence angle is absorbed by an absorber of the adapter device.

In some embodiment, the method can further comprise:

(e) capturing images of the sample in the layer of uniform thickness with the camera;

(f) analyzing the images to enumerate the analyte in the images; and (g) calculating the concentration of the analyte in the sample based on the uniform thickness, a field of view of the camera, analyte number, and a predetermined correction factor;

wherein the field of view is the extent of the field in which the camera captures the images;

wherein the correction factor is determined by a miscount ratio, which is dependent on the field of view, the uniform thickness, and properties of the analyte.

Exemplary Embodiments for WBC Measurement

For the device or method embodiments of the current invention, the device can further comprise, on one or both plates, multi reagent layers including anti-conglutination reagents, cell lysing reagents, cell staining reagents, release time control material, and any combinations thereof.

In some embodiments, each reagent layer coated on the plates has a thickness of 10 nm, 100 nm, 200 nm, 500 nm, 1 um or in a range between any two of the values.

In some embodiments, the anti-conglutination agent comprises ethylenediaminetetraacetic acid (EDTA), EDTA disodium, K2EDTA, or K3EDTA, or any combinations thereof.

In some embodiments, the cell stain agent comprises Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, or DAPI (4',6-Diamidino-2-Phenylindole, Dihydrochloride), or any combinations thereof.

In some embodiments, the cell lysing agent comprises ammonium chloride, sodium bicarbonate, ethylenediaminetetraacetic acid (EDTA), acetic acid, citric acid, or other acid and base, or any combinations thereof.

In some embodiments, the release time control material comprises albumin, carbomers, carboxymethyl cellulose, carrageenan, chitosan, dextrin, polyethylene glycol, polyvinylpyrrolidone, or polyvinyl alcohol, or any combinations thereof.

In some embodiments of the method embodiments of the current invention, the RBCs, platelets, or both are lysed in the sample before the detection and/or measurement of WBCs.

In some embodiments of the method embodiments of the current invention, the WBCs, platelets, or both are lysed in sample before the detection of RBCs.

In some embodiments of the method embodiments of the current invention, the RBCs, WBCs, or both are lysed in sample before the detection of PLTs.

Group of Other Examples of Present Invention

Further examples of inventive subject matter according to the present disclosure are described in the following enumerated paragraphs.

Correction Factor and Field of View

A1. A method for analyzing an analyte in a liquid sample, comprising:
    (a) obtaining the liquid sample;
    (b) compressing at least part of the sample into a layer of uniform thickness,
    (c) capturing images of the sample in the layer of uniform thickness with a camera, wherein the images show the analyte; and
    (d) analyzing the images to enumerate the analyte in the images,
    (e) calculating the concentration of the analyte in the sample based on the uniform thickness, a field of view of the camera, the analyte enumeration, and a predetermined correction factor;
    wherein the field of view is the extent of the field in which the camera captures the images;
    wherein the correction factor is determined by a miscount ratio, which is dependent on the field of view, the uniform thickness, and properties of the analyte.

Illumination for WBC

B1. An adapter device for analyzing an analyte in a liquid sample, comprising:
    (f) an attachment member configured to attach the adapter to an apparatus that comprises a light source and a camera;
    (g) a card slot configured to accommodate a sample card, which contains a liquid sample that is compressed into a layer of uniform thickness, wherein when the sample card inserted into the card slot, the sample is positioned under the view of the camera and the light source;
    (h) an optical filter configured to filter light from the light source to form a first beam with a specific wavelength range, wherein a part of the first beam illuminates on the edge of the sample card and travels in the sample card to illuminate the sample;
    (i) a mirror configured to deflect part of the first beam to form a second beam that back-illuminates the sample in an oblique angle;
    (j) an absorber configured to absorb a remaining part of the first beam that has a divergence angle.

B2. The adaptor of embodiment B1, wherein the lens is positioned on a front-side of the sample and the mirror is positioned to obliquely illuminate the sample from a back-side of the sample, wherein the oblique angle is larger than a collecting angle of the lens.

B3. The adaptor of embodiment B1, wherein the mirror and the optical absorber are mounted on a common structure and tilted with respect to one another.

B4. The adaptor of embodiment B1, further comprising a wavelength filter positioned between the sample and the camera to pass fluorescence emitted by the sample in response to the oblique illumination.

B5. The adaptor of embodiment B1, further comprising a rubber door to cover the sample receptacle slot to prevent ambient light from entering the optical assembly and entering the camera.

B6. The adaptor of embodiment B1, wherein the light source and the camera are positioned on the same side of the hand-held electronic device and at fixed distance to one another.

B7. The adaptor of embodiment B6, wherein the hand-held electronic device is a smart phone.

B8. The adaptor of embodiment B1, wherein the sample card is supported by a sample holder comprising a planar structure, and wherein the receptacle sample slot is configured to position the planar structure to extend partially into a path of illumination light from the light source to couple illumination light into the planar structure.

B9. The adaptor of embodiment B8, wherein the receptacle slot is configured to position the planar structure such that the path of illumination light is incident on an edge of the planar structure, wherein the edge extends along a plane that is normal to a plane comprising the field of view.

B10. The adaptor of embodiment B8, wherein the mirror is arranged to reflect the light to partially obliquely illuminate the sample from a back side of the planar structure and to partially illuminate an edge of the planar structure to couple illumination light into the planar structure.

B11 The adaptor of embodiment B8, wherein the planar structure is configured to waveguide the coupled illumination light to the sample to illuminate the sample and cause the sample to emit fluorescence.

B12. A method for analyzing an analyte in a liquid sample, comprising:
(a) obtaining the liquid sample;
(b) compressing at least part of the sample into a layer of uniform thickness with a sample card,
(c) inserting the sample card into an adaptor device, which is configured to be attached to an apparatus that comprises a light source and a camera;
(d) illuminating the sample with light from the light source, wherein
  i. the light is filtered by an optical filter of the adapter device to form a first beam with a specific wavelength range, part of the first beam illuminating on the edge of the sample card and travels in the sample card to illuminate the sample;
  ii. part of the first beam is deflected by a mirror of the adapter device to form a second beam that back-illuminates the sample in an oblique angle; and
  iii. a remaining part of the first beam that has a divergence angle is absorbed by an absorber of the adapter device.

B13. The method of embodiment B2, further comprising:
(e) capturing images of the sample in the layer of uniform thickness with the camera;
(f) analyzing the images to enumerate the analyte in the images; and
(g) calculating the concentration of the analyte in the sample based on the uniform thickness, a field of view of the camera, analyte number, and a predetermined correction factor;
wherein the field of view is the extent of the field in which the camera captures the images;
wherein the correction factor is determined by a miscount ratio, which is dependent on the field of view, the uniform thickness, and properties of the analyte.

Additional Features:

C1. The device or method of any prior embodiments, wherein the liquid sample is a blood sample.
C2. The device or method of any prior embodiments, wherein the analyte is white blood cells (WBC).
C3. The device or method of any prior embodiments, wherein the analyte is a WBC subtype.
C4. The device or method of any prior embodiments, wherein the analyte is neutrophils, eosinophils, basophils, lymphocytes, or monocytes.
C5. The device or method of any prior embodiments, wherein the analyte is marked with fluorescence.
C6. The device or method of any prior embodiments, wherein the uniform thickness is in the range of 5 to 30 um.
C7. The device or method of any prior embodiments, wherein the uniform thickness is in the range of 8 to 12 um.
C8. The device or method of any prior embodiments, wherein the uniform thickness is around 10 um.
C9. The device or method of any prior embodiments, wherein the field of view (FOV) is equal to or larger than 4 $mm^2$.
C10. The device or method of any prior embodiments, wherein the field of view (FOV) is equal to or larger than 16 $mm^2$.
C11. The device or method of any prior embodiments, wherein the field of view (FOV) is equal to or larger than 36 $mm^2$.
C12. The device or method of any prior embodiments, wherein the field of view (FOV) is equal to or larger than 64 $mm^2$.
C13. The device or method of any prior embodiments, wherein the field of view (FOV) is equal to or larger than 100 $mm^2$.
C14. The device or method of any prior embodiments, wherein the correction factor is selected with the chart:

| Sample Thickness | Correction Factor |
| --- | --- |
| 2 | 1 |
| 3 | 1 |
| 5 | 1.1 |
| 10 | 1.3 |
| 30 | 2.0 |

C15. The device or method of any prior embodiments, wherein the analyte is marked with fluorescence and the wavelength range of the first beam matches the excitation wavelength of the fluorescence marking the analyte.
C15. The device or method of any prior embodiments, wherein the adaptor device further comprises a housing member.
C16. The device or method of any prior embodiments, wherein the adaptor device further comprises a lever, which can be inserted into or extracted from the housing member.
C17. The device or method of any prior embodiments, wherein the mirror and the absorber are mounted on the lever.
C18. The device or method of any prior embodiments, wherein adaptor device comprises a card slot that has a secured opening that allows the insertion of the sample card and prevents ambient light from entering the card slot.

WBC Analysis Device

AA1. A device for analyzing white blood cells in a blood sample, comprising:
a first plate, a second plate, and spacers, wherein:
  i. the plates are movable relative to each other into different configurations;
  ii. one or both plates are flexible;
  iii. each of the plates comprises an inner surface that has a sample contact area for contacting a blood sample;
  iv. one or both of the plates comprise the spacers that are permanently fixed on the sample contact area of a respective plate;
  v. the spacers have:
    (a) a predetermined substantially uniform height that has a value selected in the range of 2 um to 30 um,
    (b) a shape of pillar with substantially uniform cross-section and a flat top surface;
    (c) a ratio of the width to the height equal to or larger than one;
    (d) a predetermined, fixed, non-random, inter-spacer distance that is in the range of 10 um to 200 um (micron);

(e) a filling factor of equal to 1% or larger, wherein the filling factor is the ratio of the spacer contact area (on the plate) to the total plate area; and (f) the filling factor multiplies the Young's modulus of the spacer is equal to 2 MPa or larger;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA2. A device for analyzing white blood cells in a blood sample, comprising:
a first plate, a second plate, spacers, and adaptor wherein:
i. the plates are movable relative to each other into different configurations;
ii. one or both plates are flexible;
iii. each of the plates comprises an inner surface that has a sample contact area for contacting a fluidic sample;
iv. one or both of the plates comprise the spacers that are permanently fixed on the sample contact area of a respective plate;
v. the spacers have:
(a) a predetermined substantially uniform height that has a value selected in the range of 2 um to 30 um,
(b) a shape of pillar with substantially uniform cross-section and a flat top surface;
(c) a ratio of the width to the height equal or larger than one;
(e) a predetermined fixed, non-random, inter-spacer distance that is in the range of 10 um to 200 um;
(e) a filling factor of equal to 1% or larger, wherein the filling factor is the ratio of the spacer contact area (on the plate) to the total plate area; and
(f) the filling factor multiplies the Young's modulus of the spacer is equal to 2 MPa or larger;
vi. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer surface of the camera, and (d) an optical system in the housing configured to have at least a part of the sample contact area be imaged by the camera;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA3. A method for analyzing white blood cells in a blood sample, comprising:
(a) obtaining a blood sample;
(b) obtaining a device of AA1 or AA2;
(c) depositing the blood sample on one or both of the plates when the plates are configured in the open configuration,
(d) after (c), forcing the two plates into a closed configuration; and
(e) capturing images of sample in the layer of uniform thickness while the plates are the closed configuration; and
(f) analyzing the images to determine the concentration of white blood cells in the sample.

AA4 A method for white blood cell and sub-type (including neutrophils, eosinophils, basophils, lymphocytes, and monocytes) counting using a single device, comprising:
(a) obtaining a blood sample;
(b) obtaining the device of any prior embodiments, wherein the spacer height is 5 um to 15 um,
(c) depositing the blood sample on one or both of the plates when the plates are configured in an open configuration;
(d) after (c), forcing the two plates into a closed configuration;
(e) capturing images of the sample in the layer of uniform thickness while the plates are the closed configuration; and
(f) analyzing the images to determine the respective number of white blood cells, neutrophils, lymphocytes, monocytes, eosinophils and basophils, through the counting of the cell number in the image and the analysis of the fluorescence color and shape for each white blood cell.

BB1. The device or method of any prior embodiments, wherein the blood sample is undiluted.

BB2. The device or method of any prior embodiments, wherein the staining and shape of white blood cell provide fluorescence color and dimension distinguish of white blood cell and its subtypes.

BB3. The device or method of any prior embodiments, wherein the device further comprises, on one or both plates, multi reagent layers including anti-conglutination, cell lysing, cell staining, release time control material layers, or their combinations.

CC1. The device or method of any prior embodiments, wherein the pillar height is in the range of 5 to 15 um, CC2. The device or method of any prior embodiments, wherein the pillar height is in the range of 8 to 12 um, CC3. The device or method of any prior embodiments, wherein the pillar height is around 10 um.

CC4. The device or method of any prior embodiments, wherein the device is configured to count the white blood cells.

CC5. The device or method of any prior embodiments, wherein the device is configured to count the white blood cells sub-types (including neutrophils, eosinophils, basophils, lymphocytes, and monocytes), CC6. The device or method of any prior embodiments, wherein spacer height is in the range of 7.5 um to 10.5 um.

CC7. The device or method of any prior embodiments, wherein spacer height is in the range of 9.5 um to 12.5 um.

CC8. The device or method of any prior embodiments, wherein spacer height is in the range of 11.5 um to 13.5 um.

CC9. The device or method of any prior embodiments, wherein spacer height is in the range of 12.5 um to 14.5 um.

CC10. The device or method of any prior embodiments, wherein spacer height is in the range of 13.5 um to 16 um.

CC11. The device or method of any prior embodiments, wherein a preferred field of view for counting and differentiating WBCs is 0.1 mm², 10 mm², 50 mm², 100 mm² or a range between any two of the values;

CC12. The device or method of any prior embodiments, wherein when the gap size of device is 10 um, the FoV is larger than 36 mm², thereby the WBC counting and differentiate accuracy is less than 5%.

CC13. The device or method of any prior embodiments, wherein when the gap size of device is 10 um, the FoV is larger than 16 mm², thereby the WBC counting and differentiate accuracy is less than 10%.

CC14. The device or method of any prior embodiments, wherein when the gap size of device is 10 um, the FoV is larger than 2 mm², thereby the WBC counting and differentiate accuracy is less than 20%.

CC15. The device or method of any prior embodiments, wherein a field of view is 0.1 mm² to 10 mm², preferred gap size of device is in the range of 10 um to 30 um, 30 um to 50 um, thereby the counting and differentiate accuracy is less than 10%.

CC16. The device or method of any prior embodiments, wherein field of view is 0.1 mm² to 10 mm², preferred gap size of device is in the range of 10 um to 30 um, thereby the counting and differentiate accuracy is less than 20%.

CC17. The device or method of any prior embodiments, wherein field of view is 10 mm² to 50 mm², preferred gap size of device is in the range of 5 um to 10 um, 10 um to 30 um, thereby the counting and differentiate accuracy is less than 10%.

CC18. The device or method of any prior embodiments, wherein field of view is 10 mm² to 50 mm², preferred gap size of device is in the range of 2 um to 5 um, 5 um to 10 um, 10 um to 30 um, thereby the counting and differentiate accuracy is less than 20%.

CC19. The device or method of any prior embodiments, wherein field of view is field of view of 50 mm² to 100 mm², preferred gap size of device is in the range of 2 um to 5 um, 5 um to 10 um, 10 um to 30 um, 30 um to 50 um thereby the counting and differentiate accuracy is less than 10%.

CC20. The device or method of any prior embodiments, wherein the spacer has a height in the range of 2 um to 5 um, thereby the WBCs missing counting is less than 15%.

CC21. The device or method of any prior embodiments, wherein the spacer has a height in the range of 2 um to 5 um, 5 um to 10 um, thereby the WBCs missing counting is less than 30%.

CC22. The device or method of any prior embodiments, wherein the spacer has a height of preferred range of 2 um to 5 um, 5 um to 10 um, 10 um to 30 um thereby the WBCs missing counting is less than 60%.

CC23. The device or method of any prior embodiments, wherein the sample to phone lens distance is in the range of 2 mm to 5 mm.

CC24. The device or method of any prior embodiments, wherein the sample to phone lens distance is in the range of 4 mm to 7 mm.

CC25. The device or method of any prior embodiments, wherein the sample to phone lens distance is in the range of 6 mm to 9 mm.

CC26. The device or method of any prior embodiments, wherein the sample to phone lens distance is in the range of 8 mm to 11 mm.

CC27. The device or method of any prior embodiments, wherein the sample to phone lens distance is in the range of 10 mm to 13 mm.

CC28. The device or method of any prior embodiments, wherein the sample to phone lens distance is in the range of 12 mm to 15 mm.

Imaging Analysis by Artificial Intelligence and Machine Learning

In certain embodiments of the present disclosure, the sample deposition is a deposition directly from a subject to the plate without using any transferring devices. In certain embodiments, during the deposition, the amount of the sample deposited on the plate is unknown.

In certain embodiments, the method further comprises an analyzing that analyze the sample. In certain embodiments, the analyzing comprises calculating the volume of a relevant sample volume by measuring the lateral area of the relevant sample volume and calculating the volume from the lateral area and the predetermined spacer height. In certain embodiments, the pH value at location of a sample that is between the two plates in a closed configuration is determined by the volume of the location and by analyzing an image(s) taken from that location. In certain embodiments, the determination by analyzing an image uses artificial intelligence and machine learning Artificial Intelligence and/or Machine Learning to Improve Imaging In certain embodiments of the present invention, the images taken during an assay operation and/or the samples measured by an assay are analyzed by artificial intelligence and machine learning. The samples include, but not limited to, medical samples, biology samples, environmental samples and chemistry samples.

In certain embodiments of the present invention, the sample is held by a QMAX device. The QMAX device together with imaging plus artificial intelligence and/or machine learning can overcome certain limitations in prior arts.

One important aspect of the present invention is to provide a machine learning framework to enhance the functionality, application scope and the accuracy in assaying using QMAX device, especially when a computer program is used.

In certain embodiments of the present invention, a device and a method for assaying sample and/or assay operation (e.g. tracking label identification) that utilizes QMAX together with imaging plus a machine learning and/or artificial intelligence comprises:

(1) using a QMAX device that has an auxiliary structure in the form of pillars to precisely control the distribution and volume of the sample in assaying, wherein the sample for assaying is loaded into the QMAX device and is kept between the two parallel plates on the QMAX device with an upper plate being transparent for imaging by an imager;

(2) the gap between the two parallel plates in the QMAX device is spaced narrowly—with the distance of the gap being proportional to the size of the analytes to be assayed—by which the analytes in the sample form a single layer between the said plates that can be imaged by an imager on the QMAX device;

(3) the sample volume corresponding to the AoI (area-of-interest) on the upper plate of the QMAX device can be precisely characterized by AoI and the gap—because the uniformity of the gap between the plates in the QMAX device;

(4) the image on the sample for assaying sandwiched between the AoI x gap in the QMAX device is a pseudo-2D image, because it has the appearance of a 2D image, but it is an image of a 3D sample with its depth being known priori or characterized through other means;

(5) the captured pseudo-2D sample image taken over the AoI of the QMAX device can characterize the location of the analytes, color, shape, counts, and concentration of the analytes in the sample for assaying;

(6) based on abovementioned properties, the captured pseudo-2D image of QMAX device for assaying is amendable to a machine learning framework that applies to analyte detection, localization, identification, segmentation, counting, etc. for assaying in various applications; or (7) any combination of thereof.

In certain embodiments of the present invention, a machine learning framework for QMAX based devices are implemented into a device that is capable of running an algorithms such as deep learning to discriminatively locate, identify, segment and count analytes (e.g. blood cells) based on the pseudo-2D image captured by the QMAX imager.

In certain embodiments of the present invention, the machine learning improves the images captured by the imager on the QMAX device and reduces the effects of noise and artifacts—including and not limited to air bobbles, dusts, shadows, and pillars.

In certain embodiments of the present invention, the training of machine learning uses the spacers of the QMAX card to reduce the data size of training set.

Approach 1—Deep Learning Approach

In certain embodiments, deep learning is used, whereinthe analyte detection and localization workflow consists of two stages, training and prediction.

(i) Training Stage

At the training stage of the present invention, training data with annotation is fed into a convolutional neural network. Convolutional neural network is a specialized neural network for processing data that has a grid-like, feed forward and layered network topology. Examples of the data include time-series data, which can be thought of as a 1D grid taking samples at regular time intervals, and image data, which can be thought of as a 2D grid of pixels. Convolutional networks have been successful in practical applications. The name "convolutional neural network" indicates that the network employs a mathematical operation called convolution. Convolution is a specialized kind of linear operation. Convolutional networks are simply neural networks that use convolution in place of general matrix multiplication in at least one of their layers.

In training the machine learning model in some embodiments of the present invention, it receives one or multiple images of samples that contain the analytes taken by the imager over the sample holding QMAX device as training data. Training data are annotated for analytes to be assayed, wherein the annotations indicate whether or not analytes are in the training data and where they locate in the image. Annotation can be done in the form of tight bounding boxes which fully contains the analyte, or center locations of analytes. In the latter case, center locations are further converted into circles covering analytes or a Gaussian kernel in a point map.

When the size of training data is large, training machine learning model presents two challenges: annotation (usually done by human) is time consuming, and the training is computationally expensive. To overcome these challenges, one can partition the training data into patches of small size, then annotate and train on these patches, or a portion of these patches. The term "machine learning" refers to algorithms, systems and apparatus in the field of artificial intelligence that often use statistical techniques and artificial neural network trained from data without being explicitly programmed.

In some embodiments of the present invention, the annotated images are fed to the machine learning (ML) training module, and the model trainer in the machine learning module will train a ML model from the training data (annotated sample images). The input data will be fed to the model trainer in multiple iterations until certain stopping criterion is satisfied. The output of the ML training module is a ML model—a computational model that is built from a training process in the machine learning from the data that gives computer the capability to perform certain tasks (e.g. detect and classify the objects) on its own.

The trained machine learning model is applied during the predication (or inference) stage by the computer. Examples of machine learning models include ResNet, DenseNet, etc. which are also named as "deep learning models" because of the depth of the connected layers in their network structure. In some embodiments, the Caffe library with fully convolutional network (FCN) was used for model training and predication, and other convolutional neural network architecture and library can also be used, such as TensorFlow.

The training stage generates a model that will be used in the prediction stage. The model can be repeatedly used in the prediction stage for assaying the input. Thus, the computing unit only needs access to the generated model. It does not need access to the training data, nor requiring the training stage to be run again on the computing unit.

(ii) Prediction Stage

In the predication/inference stage, a detection component is applied to the input image, and an input image is fed into the predication (inference) module preloaded with a trained model generated from the training stage. The output of the prediction stage can be bounding boxes that contain the detected analytes with their center locations or a point map indicating the location of each analyte, or a heatmap that contains the information of the detected analytes.

When the output of the prediction stage is a list of bounding boxes, the number of analytes in the image of the sample for assaying is characterized by the number of detected bounding boxes. When the output of the prediction stage is a point map, the number of analytes in the image of the sample for assaying is characterized by the integration of the point map. When the output of the prediction is a heatmap, a localization component is used to identify the location and the number of detected analytes is characterized by the entries of the heatmap.

One embodiment of the localization algorithm is to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

In the detection component using heatmap, an input image, along with the model generated from the training stage, is fed into a convolutional neural network, and the output of the detection stage is a pixel-level prediction, in the form of a heatmap. The heatmap can have the same size as the input image, or it can be a scaled down version of the input image, and it is the input to the localization component. We disclose an algorithm to localize the analyte center. The main idea is to iteratively detect local peaks from the heatmap. After the peak is localized, we calculate the local area surrounding the peak but with smaller value. We remove this region from the heatmap and find the next peak from the remaining pixels. The process is repeated only all pixels are removed from the heatmap.

In certain embodiments, the present invention provides the localization algorithm to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

---
Algorithm GlobalSearch (heatmap)
---
Input:
    heatmap
Output:
    loci
loci ←{ }
sort(heatmap)
while (heatmap is not empty) {
    s ← pop(heatmap)
    D ← {disk center as s with radius R}
    heatmap = heatmap \ D // remove D from the heatmap
    add s to loc}
---

After sorting, heatmap is a one-dimensional ordered list, where the heatmap value is ordered from the highest to the lowest. Each heatmap value is associated with its corresponding pixel coordinates. The first item in the heatmap is the one with the highest value, which is the output of the pop(heatmap) function. One disk is created, where the center is the pixel coordinate of the one with highest heatmap value. Then all heatmap values whose pixel coordinates resides inside the disk is removed from the heatmap. The algorithm repeatedly pops up the highest value in the current heatmap, removes the disk around it, till the items are removed from the heatmap.

In the ordered list heatmap, each item has the knowledge of the proceeding item, and the following item. When removing an item from the ordered list, we make the following changes:

Assume the removing item is $x_r$, its proceeding item is $x_p$, and its following item is $x_f$.

For the proceeding item $x_p$, re-define its following item to the following item of the removing item. Thus, the following item of $x_p$ is now $x_f$.

For the removing item $x_r$, un-define its proceeding item and following item, which removes it from the ordered list.

For the following item $x_f$, re-define its proceeding item to the proceeding item of the removed item. Thus, the proceeding item of $x_f$ is now $x_p$.

After all items are removed from the ordered list, the localization algorithm is complete. The number of elements in the set loci will be the count of analytes, and location information is the pixel coordinate for each s in the set loci.

Another embodiment searches local peak, which is not necessary the one with the highest heatmap value. To detect each local peak, we start from a random starting point, and search for the local maximal value. After we find the peak, we calculate the local area surrounding the peak but with smaller value. We remove this region from the heatmap and find the next peak from the remaining pixels. The process is repeated only all pixels are removed from the heatmap.

---
Algorithm LocalSearch (s, heatmap)
---
Input:
    s: starting location (x, y)
    heatmap
Output:
    s: location of local peak.
We only consider pixels of value > 0.
Algorithm Cover (s, heatmap)
Input:
    s: location of local peak.
    heatmap:
Output:
    cover: a set of pixels covered by peak:
---

This is a breadth-first-search algorithm starting from s, with one altered condition of visiting points: a neighbor p of the current location q is only added to cover if heatmap[p]>0 and heatmap[p]<=heatmap[q]. Therefore, each pixel in cover has a non-descending path leading to the local peak s.

---
Algorithm Localization (heatmap)
---
Input:
    heatmap
Output:
    loci
loci ←{ }
pixels ←{all pixels from heatmap}
while pixels is not empty {
    s ←any pixel from pixels
    s ←LocalSearch(s, heatmap)   // s is now local peak
    probe local region of radius R surrounding s for better local peak
    r ←Cover(s, heatmap)
    pixels ← pixels \ r     // remove all pixels in cover
    add s to loci
---

In certain embodiments, the image analysis comprising a Combination of Deep Learning and Computer Vision Approach, wherein I the detection and localization are realized by computer vision algorithms, and a classification is realized by deep learning algorithms, wherein the computer vision algorithms detect and locate possible candidates of analytes, and the deep learning algorithm classifies each possible candidate as a true analyte and false analyte. The location of all true analyte (along with the total count of true analytes) will be recorded as the output.

Detection. The computer vision algorithm detects possible candidate based on the characteristics of analytes, including but not limited to intensity, color, size, shape, distribution, etc. A pre-processing scheme can improve the detection. Pre-processing schemes include contrast enhancement, histogram adjustment, color enhancement, de-nosing, smoothing, de-focus, etc. After pre-processing, the input image is sent to a detector. The detector tells the existing of possible candidate of analyte and gives an estimate of its location. The detection can be based on the analyte structure (such as edge detection, line detection, circle detection, etc.), the connectivity (such as blob detection, connect components, contour detection, etc.), intensity, color, shape using schemes such as adaptive thresholding, etc.

Localization After detection, the computer vision algorithm locates each possible candidate of analytes by providing its boundary or a tight bounding box containing it. This can be achieved through object segmentation algorithms, such as adaptive thresholding, background subtraction, floodfill, mean shift, watershed, etc. Very often, the localization can be combined with detection to produce the detection results along with the location of each possible candidates of analytes.

Classification, the deep learning algorithms, such as convolutional neural networks, achieve start-of-the-art visual classification. We employ deep learning algorithms for classification on each possible candidate of analytes. Various convolutional neural network can be utilized for analyte classification, such as VGGNet, ResNet, MobileNet, DenseNet, etc.

Given each possible candidate of analyte, the deep learning algorithm computes through layers of neurons via convolution filters and non-linear filters to extract high-level features that differentiate analyte against non-analytes. A layer of fully convolutional network will combine high-level features into classification results, which tells whether it is a true analyte or not, or the probability of being an analyte.

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less than 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm² (centimeter square) to 100 kg/cm², (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

Example of Present Embodiments $IDS^4/hE$

In certain embodiments of the present disclosure, a device for forming a thin fluidic sample layer with a uniform predetermined thickness by pressing can comprise a first plate. In certain embodiments of the present disclosure, a device for forming a thin fluidic sample layer with a uniform predetermined thickness by pressing can comprise a second plate. In certain embodiments of the present disclosure, a device for forming a thin fluidic sample layer with a uniform predetermined thickness by pressing can comprise spacers. In certain embodiments, the plates are movable relative to each other into different configurations. In certain embodiments, one or both plates are flexible. In certain embodiments, each of the plates comprises an inner surface that has a sample contact area for contacting a fluidic sample. In certain embodiments, each of the plates comprises, on its respective outer surface, a force area for applying a pressing force that forces the plates together. In certain embodiments, one or both of the plates comprise the spacers that are permanently fixed on the inner surface of a respective plate. In certain embodiments, the spacers have a predetermined substantially uniform height that is equal to or less than 200 microns, and a predetermined fixed inter-spacer-distance. In certain embodiments, the fourth power of the inter-spacer-distance (ISD) divided by the thickness (h) and the Young's modulus (E) of the flexible plate ($ISD^4/(hE)$) is $5 \times 10^6$ um³/GPa or less. In certain embodiments, at least one of the spacers is inside the sample contact area. In certain embodiments, one of the configurations is an open configuration, in which: the two plates are partially or completely separated apart, the spacing between the plates is not regulated by the spacers, and the sample is deposited on one or both of the plates. In certain embodiments, another of the configurations is a closed configuration which is configured after the sample is deposited in the open configuration and the plates are forced to the closed configuration by applying the pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

In certain embodiments of the present disclosure, a method of forming a thin fluidic sample layer with a uniform predetermined thickness by pressing can comprise obtaining a device of the present disclosure. In certain embodiments of the present disclosure, a method of forming a thin fluidic sample layer with a uniform predetermined thickness by pressing can comprise depositing a fluidic sample on one or both of the plates when the plates are configured in an open configuration. In certain embodiments, the open configuration is a configuration in which the two plates are partially or completely separated apart and the spacing between the plates is not regulated by the spacers. In certain embodiments of the present disclosure, a method of forming a thin fluidic sample layer with a uniform predetermined thickness by pressing can comprise forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

In certain embodiments of the present disclosure, a device for analyzing a fluidic sample can comprise a first plate. In certain embodiments of the present disclosure, a device for analyzing a fluidic sample can comprise a second plate. In certain embodiments of the present disclosure, a device for analyzing a fluidic sample can comprise spacers. In certain embodiments, the plates are movable relative to each other into different configurations. In certain embodiments, one or both plates are flexible. In certain embodiments, each of the plates has, on its respective inner surface, a sample contact area for contacting a fluidic sample. In certain embodiments, one or both of the plates comprise the spacers and the spacers are fixed on the inner surface of a respective plate. In certain embodiments, the spacers have a predetermined substantially uniform height that is equal to or less than 200 microns, and the inter-spacer-distance is predetermined. In certain embodiments, the Young's modulus of the spacers multiplied by the filling factor of the spacers is at least 2 MPa. In certain embodiments, at least one of the spacers is inside the sample contact area. In certain embodiments, one of the configurations is an open configuration, in which: the two plates are partially or completely separated apart, the spacing between the plates is not regulated by the spacers, and the sample is deposited on one or both of the plates. In certain embodiments, another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

In certain embodiments of the present disclosure, a method of forming a thin fluidic sample layer with a uniform predetermined thickness by pressing can comprise obtaining a device of the present disclosure. In certain embodiments of the present disclosure, a method of forming a thin fluidic sample layer with a uniform predetermined thickness by pressing can comprise depositing a fluidic sample on one or both of the plates when the plates are configured in an open configuration. In certain embodiments, the open configuration is a configuration in which the two plates are partially or completely separated apart and the spacing between the plates is not regulated by the spacers. In certain embodiments of the present disclosure, a method of forming a thin fluidic sample layer with a uniform predetermined thickness by pressing can comprise forcing the two plates into a closed configuration. In certain embodiments, at least part of the sample is compressed by the two plates into a layer of substantially uniform thickness, wherein the uniform thickness of the layer is confined by the sample contact surfaces of the plates and is regulated by the plates and the spacers.

In certain embodiments of the present disclosure, a device for analyzing a fluidic sample can comprise a first plate. In certain embodiments of the present disclosure, a device for analyzing a fluidic sample can comprise a second plate. In certain embodiments, the plates are movable relative to each other into different configurations. In certain embodiments, one or both plates are flexible. In certain embodiments, each of the plates has, on its respective surface, a sample contact area for contacting a sample that contains an analyte. In certain embodiments, one or both of the plates comprise spacers that are permanently fixed to a plate within a sample contact area, wherein the spacers have a predetermined substantially uniform height and a predetermined fixed inter-spacer distance that is at least about 2 times larger than the size of the analyte, up to 200 um, and wherein at least one of the spacers is inside the sample contact area. In certain embodiments, one of the configurations is an open configuration, in which: the two plates are separated apart, the spacing between the plates is not regulated by the spacers, and the sample is deposited on one or both of the plates. In certain embodiments, another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

In certain embodiments of the present disclosure, a method of forming a thin fluidic sample layer with a uniform predetermined thickness by pressing can comprise obtaining a device of the present disclosure. In certain embodiments of the present disclosure a method of forming a thin fluidic sample layer with a uniform predetermined thickness by pressing can comprise depositing a fluidic sample on one or both of the plates; when the plates are configured in an open configuration, wherein the open configuration is a configuration in which the two plates are partially or completely separated apart and the spacing between the plates is not regulated by the spacers. In certain embodiments of the present disclosure a method of forming a thin fluidic sample layer with a uniform predetermined thickness by pressing can comprise forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

In certain embodiments of the present disclosure, a device for forming a thin fluidic sample layer with a uniform predetermined thickness by pressing can comprise a first plate. In certain embodiments of the present disclosure, a device for forming a thin fluidic sample layer with a uniform predetermined thickness by pressing can comprise a second plate. In certain embodiments of the present disclosure, a device for forming a thin fluidic sample layer with a uniform predetermined thickness by pressing can comprise spacers. In certain embodiments, the plates are movable relative to each other into different configurations. In certain embodiments, one or both plates are flexible. In certain embodiments, each of the plates comprises, on its respective inner surface, a sample contact area for contacting and/or compressing a fluidic sample. In certain embodiments, each of the plates comprises, on its respective outer surface, an area for applying a force that forces the plates together. In certain embodiments, one or both of the plates comprise the spacers that are permanently fixed on the inner surface of a respective plate. In certain embodiments, the spacers have a predetermined substantially uniform height that is equal to or less than 200 microns, a predetermined width, and a predetermined fixed inter-spacer-distance. In certain embodiments, a ratio of the inter-spacer-distance to the spacer width is 1.5 or larger. In certain embodiments, at least one of the spacers is inside the sample contact area. In certain embodiments, one of the configurations is an open configuration, in which: the two plates are partially or completely separated apart, the spacing between the plates is not regulated by the spacers, and the sample is deposited on one or both of the plates. In certain embodiments, another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

In certain embodiments of the present disclosure, a method of forming a thin fluidic sample layer with a uniform predetermined thickness by pressing with an imprecise pressing force can comprise obtaining a device of the present disclosure. In certain embodiments of the present disclosure, a method of forming a thin fluidic sample layer with a uniform predetermined thickness by pressing with an imprecise pressing force can comprise obtaining a fluidic sample. In certain embodiments of the present disclosure, a method of forming a thin fluidic sample layer with a uniform predetermined thickness by pressing with an imprecise pressing force can comprise depositing the sample on one or both of the plates; when the plates are configured in an open configuration, wherein the open configuration is a configuration in which the two plates are partially or completely separated apart and the spacing between the plates is not regulated by the spacers. In certain embodiments of the present disclosure, a method of forming a thin fluidic sample layer with a uniform predetermined thickness by pressing with an imprecise pressing force can comprise forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

In certain embodiments, the spacers have a shape of pillar with a foot fixed on one of the plates and a flat top surface for contacting the other plate. In certain embodiments, the spacers have a shape of pillar with a foot fixed on one of the plates, a flat top surface for contacting the other plate, substantially uniform cross-section. In certain embodiments, the spacers have a shape of pillar with a foot fixed on one of the plates and a flat top surface for contacting the other plate, wherein the flat top surface of the pillars has a variation in less than 10 nm. In certain embodiments, the spacers have a shape of pillar with a foot fixed on one of the plates and a flat top surface for contacting the other plate, wherein the flat top surface of the pillars has a variation in less than 50 nm. In certain embodiments, the spacers have a shape of pillar with a foot fixed on one of the plates and a flat top surface for contacting the other plate, wherein the flat top surface of the pillars has a variation in less than 50 nm. In certain embodiments, the spacers have a shape of pillar with a foot fixed on one of the plates and a flat top surface for contacting the other plate, wherein the flat top surface of the pillars has a variation in less than 10 nm, 20 nm, 30 nm, 100 nm, 200 nm, or in a range of any two of the values.

In certain embodiments, the Young's modulus of the spacers multiplied by the filling factor of the spacers is at least 2 MPa. In certain embodiments, the sample comprises an analyte and the predetermined constant inter-spacer distance is at least about 2 times larger than the size of the analyte, up to 200 um. In certain embodiments, the sample comprise an analyte, the predetermined constant inter-spacer distance is at least about 2 times larger than the size of the analyte, up to 200 um, and the Young's modulus of the spacers multiplied by the filling factor of the spacers is at least 2 MPa.

In certain embodiments, a fourth power of the inter-spacer-distance (IDS) divided by the thickness (h) and the Young's modulus (E) of the flexible plate (ISD^4/(hE)) is 5×10^6 um^3/GPa or less. In certain embodiments, a fourth power of the inter-spacer-distance (IDS) divided by the thickness and the Young's modulus of the flexible plate (ISD^4/(hE)) is 1×10^6 um^3/GPa or less. In certain embodiments, a fourth power of the inter-spacer-distance (IDS) divided by the thickness and the Young's modulus of the flexible plate (ISD^4/(hE)) is 5×10^5 um^3/GPa or less. In certain embodiments, the Young's modulus of the spacers multiplied by the filling factor of the spacers is at least 2 MPa, and a fourth power of the inter-spacer-distance (IDS) divided by the thickness and the Young's modulus of the flexible plate (ISD^4/(hE)) is 1×10^5 um^3/GPa or less. In certain embodiments, the Young's modulus of the spacers multiplied by the filling factor of the spacers is at least 2 MPa, and a fourth power of the inter-spacer-distance (IDS) divided by the thickness and the Young's modulus of the flexible plate (ISD^4/(hE)) is 1×10^4 um^3/GPa or less. In certain embodiments, the Young's modulus of the spacers multiplied by the filling factor of the spacers is at least 20 MPa.

In certain embodiments of the present disclosure, the ratio of the inter-spacing distance of the spacers to the average width of the spacer is 2 or larger. In certain embodiments, the ratio of the inter-spacing distance of the spacers to the average width of the spacer is 2 or larger, and the Young's modulus of the spacers multiplied by the filling factor of the spacers is at least 2 MPa. In certain embodiments, the inter-spacer distance that is at least about 2 times larger than the size of the analyte, up to 200 um. In certain embodiments, a ratio of the inter-spacer-distance to the spacer width is 1.5 or larger. In certain embodiments, a ratio of the width to the height of the spacer is 1 or larger. In certain embodiments, a ratio of the width to the height of the spacer is 1.5 or larger. In certain embodiments, a ratio of the width to the height of the spacer is 2 or larger. In certain embodiments, a ratio of the width to the height of the spacer is larger than 2, 3, 5, 10, 20, 30, 50, or in a range of any two the value.

In certain embodiments, a force that presses the two plates into the closed configuration is an imprecise pressing force. In certain embodiments, a force that presses the two plates into the closed configuration is an imprecise pressing force provided by human hand. In certain embodiments, the forcing of the two plates to compress at least part of the sample into a layer of substantially uniform thickness comprises a use of a conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample. In certain embodiments, the pressing force is an imprecise force that has a magnitude which is, at the time that the force is applied, either (a) unknown and unpredictable, or (b) cannot be known and cannot be predicted within an accuracy equal or better than 20% of the average pressing force applied. In certain embodiments, the pressing force is an imprecise force that has a magnitude which is, at the time that the force is applied, either (a) unknown and unpredictable, or (b) cannot be known and cannot be predicted within an accuracy equal or better than 30% of the average pressing force applied. In certain embodiments, the pressing force is an imprecise force that has a magnitude which is, at the time that the force is applied, either (a) unknown and unpredictable, or (b) cannot be known and cannot be predicted within an accuracy equal or better than 30% of the average pressing force applied; and wherein the layer of highly uniform thickness has a variation in thickness uniform of 20% or less. In certain embodiments, the pressing force is an imprecise force that has a magnitude which cannot, at the time that the force is applied, be determined within an accuracy equal or better than 30%, 40%, 50%, 70%, 100%, 200%, 300%, 500%, 1000%, 2000%, or in a range between any of the two values.

In certain embodiments of the present disclosure, the flexible plate has a thickness of in the range of 10 um to 200 um. In certain embodiments, the flexible plate has a thickness of in the range of 20 um to 100 um. In certain embodiments, the flexible plate has a thickness of in the range of 25 um to 180 um. In certain embodiments, the flexible plate has a thickness of in the range of 200 um to 260 um. In certain embodiments, the flexible plate has a thickness of equal to or less than 250 um, 225 um, 200 um, 175 um, 150 um, 125 um, 100 um, 75 um, 50 um, 25 um, 10 um, 5 um, 1 um, or in a range between the two of the values. In certain embodiments, the sample has a viscosity in the range of 0.1 to 4 (mPa s). In certain embodiments, the flexible plate has a thickness of in the range of 200 um to 260 um. In certain embodiments, the flexible plate has a thickness in the range of 20 um to 200 um and Young's modulus in the range 0.1 to 5 GPa.

In certain embodiments of the present disclosure, the sample deposition is a deposition directly from a subject to the plate without using any transferring devices. In certain embodiments, during the deposition, the amount of the sample deposited on the plate is unknown. In certain embodiments, the method further comprises an analyzing that analyze the sample. In certain embodiments, the analyzing comprises calculating the volume of a relevant sample volume by measuring the lateral area of the relevant sample volume and calculating the volume from the lateral area and the predetermined spacer height. In certain embodiments, the pH value at location of a sample that is between the two plates in a closed configuration is determined by the volume of the location and by analyzing an image(s) taken from that location. In certain embodiments, the determination by analyzing an image uses artificial intelligence and machine learning.

In certain embodiments, the analyzing step (e) comprises measuring: i. imaging, ii. luminescence selected from photoluminescence, electroluminescence, and electrochemiluminescence, iii. surface Raman scattering, iv. electrical impedance selected from resistance, capacitance, and inductance, or v. any combination of i-iv. In certain embodiments, the analyzing comprises reading, image analysis, or counting of the analyte, or a combination of thereof. In certain embodiments, the sample contains one or plurality of analytes, and one or both plate sample contact surfaces comprise one or a plurality of binding sites that each binds and immobilize a respective analyte. In certain embodiments, one or both plate sample contact surfaces comprise one or a plurality of storage sites that each stores a reagent or reagents, wherein the reagent(s) dissolve and diffuse in the sample. In certain embodiments, one or both plate sample contact surfaces comprises one or a plurality of amplification sites that are each capable of amplifying a signal from the analyte or a label of the analyte when the analyte or label is within 500 nm from an amplification site. In certain embodiments, i. one or both plate sample contact surfaces comprise one or a plurality of binding sites that each binds and immobilize a respective analyte; or ii. one or both plate sample contact surfaces comprise, one or a plurality of storage sites that each stores a reagent or reagents; wherein the reagent(s) dissolve and diffuse in the sample, and wherein the sample contains one or plurality of analytes; or iii. one or a plurality of amplification sites that are each capable of amplifying a signal from the analyte or a label of the analyte when the analyte or label is 500 nm from the amplification site; or iv. any combination of i to iii.

In certain embodiments, the liquid sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

In certain embodiments, the layer of uniform thickness in the closed configuration is less than 150 um. In certain embodiments, the pressing is provided by a pressured liquid, a pressed gas, or a conformal material. In certain embodiments, the analyzing comprises counting cells in the layer of uniform thickness. In certain embodiments, the analyzing comprises performing an assay in the layer of uniform thickness. In certain embodiments, In certain embodiments, the assay is a binding assay or biochemical assay. In certain embodiments, the sample deposited has a total volume less 0.5 uL. In certain embodiments, multiple drops of sample are deposited onto one or both of the plates.

In certain embodiments, the inter-spacer distance is in the range of 1 μm to 120 μm. In certain embodiments, the inter-spacer distance is in the range of 120 μm to 50 μm. In certain embodiments, the inter-spacer distance is in the range of 120 μm to 200 μm. In certain embodiments, the flexible plates have a thickness in the range of 20 um to 250 um and Young's modulus in the range 0.1 to 5 GPa. In certain embodiments, for a flexible plate, the thickness of the flexible plate times the Young's modulus of the flexible plate is in the range 60 to 750 GPa-um.

In certain embodiments, the layer of uniform thickness sample is uniform over a lateral area that is at least 1 $mm^2$. In certain embodiments, the layer of uniform thickness sample is uniform over a lateral area that is at least 3 $mm^2$. In certain embodiments, the layer of uniform thickness sample is uniform over a lateral area that is at least 5 $mm^2$. In certain embodiments, In certain embodiments, the layer of uniform thickness sample is uniform over a lateral area that is at least 10 $mm^2$. In certain embodiments, the layer of uniform thickness sample is uniform over a lateral area that is at least 20 $mm^2$. In certain embodiments, the layer of uniform thickness sample is uniform over a lateral area that is in a range of 20 mm$^2$ to 100 mm$^2$. In certain embodiments, the layer of uniform thickness sample has a thickness uniformity of up to +/−5% or better. In certain embodiments, the layer of uniform thickness sample has a thickness uniformity of up to +/−10% or better. In certain embodiments, the layer of uniform thickness sample has a thickness uniformity of up to +/−20% or better. In certain embodiments, the layer of uniform thickness sample has a thickness uniformity of up to +/−30% or better. In certain embodiments, the layer of uniform thickness sample has a thickness uniformity of up to +/−40% or better. In certain embodiments, the layer of uniform thickness sample has a thickness uniformity of up to +/−50% or better.

In certain embodiments, the spacers are pillars with a cross-sectional shape selected from round, polygonal, circular, square, rectangular, oval, elliptical, or any combination of the same. In certain embodiments, the spacers have pillar shape, have a substantially flat top surface, and have substantially uniform cross-section, wherein, for each spacer, the ratio of the lateral dimension of the spacer to its height is at least 1. In certain embodiments, the inter spacer distance is periodic. In certain embodiments, the spacers have a filling factor of 1% or higher, wherein the filling factor is the ratio of the spacer contact area to the total plate area. In certain embodiments, the Young's modulus of the spacers times the filling factor of the spacers is equal or larger than 20 MPa, wherein the filling factor is the ratio of the spacer contact area to the total plate area. In certain embodiments, the spacing between the two plates at the closed configuration is in less 200 um. In certain embodiments, the spacing between the two plates at the closed configuration is a value selected from between 1.8 um and 3.5 um. In certain embodiments, the spacing are fixed on a plate by directly embossing the plate or injection molding of the plate. In certain embodiments, the materials of the plate and the spacers are selected from polystyrene, PMMA, PC, COC, COP, or another plastic. In certain embodiments, the spacers have a pillar shape, and the sidewall corners of the spacers have a round shape with a radius of curvature at least 1 μm. In certain embodiments, the spacers have a density of at least 1000/mm$^2$. In certain embodiments, at least one of the plates is transparent. In certain embodiments, the mold used to make the spacers is fabricated by a mold containing features that are fabricated by either (a) directly reactive ion etching or ion beam etched or (b) by a duplication or multiple duplication of the features that are reactive ion etched or ion beam etched.

In certain embodiments, the spacers are configured, such that the filling factor is in the range of 1% to 5%. In certain embodiments, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%. In certain embodiments, the spacers are configured, such that the filling factor is in the range of 1% to 5%. In certain embodiments, the spacers are configured, such that the filling factor is in the range of 5% to 10%. In certain embodiments, the spacers are configured, such that the filling factor is in the range of 10% to 20%. In certain embodiments, the spacers are configured, such that the filling factor is in the range of 20% to 30%. In certain embodiments, the spacers are configured, such that the filling factor is 5%, 10%, 20%, 30%, 40%, 50%, or in a range of any two of the values. In certain embodiments, the spacers are configured, such that the filling factor is 50%, 60%, 70%, 80%, or in a range of any two of the values.

In certain embodiments, the spacers are configured, such that the filling factor multiplies the Young's modulus of the spacer is in the range of 2 MPa and 10 MPa. In certain embodiments, the spacers are configured, such that the filling factor multiplies the Young's modulus of the spacer is in the range of 10 MPa and 20 MPa. In certain embodiments, the spacers are configured, such that the filling factor multiplies the Young's modulus of the spacer is in the range of 20 MPa and 40 MPa. In certain embodiments, the spacers are configured, such that the filling factor multiplies the Young's modulus of the spacer is in the range of 40 MPa and 80 MPa. In certain embodiments, the spacers are configured, such that the filling factor multiplies the Young's modulus of the spacer is in the range of 80 MPa and 120 MPa. In certain embodiments, the spacers are configured, such that the filling factor multiplies the Young's modulus of the spacer is in the range of 120 MPa to 150 MPa.

In certain embodiments, the device further comprises a dry reagent coated on one or both plates. In certain embodiments, the device further comprises, on one or both plates, a dry binding site that has a predetermined area, wherein the dry binding site binds to and immobilizes an analyte in the sample. In certain embodiments, the device further comprises, on one or both plates, a releasable dry reagent and a release time control material that delays the time that the releasable dry regent is released into the sample. In certain embodiments, the release time control material delays the time that the dry regent starts is released into the sample by at least 3 seconds. In certain embodiments, the regent comprises anticoagulant and/or staining reagent(s). In certain embodiments, the reagent comprises cell lysing reagent(s). In certain embodiments, the device further comprises, on one or both plates, one or a plurality of dry binding sites and/or one or a plurality of reagent sites. In certain embodiments, the analyte comprises a molecule (e.g., a protein, peptides, DNA, RNA, nucleic acid, or other molecule), cells, tissues, viruses, and nanoparticles with different shapes. In certain embodiments, the analyte comprises white blood cells, red blood cells and platelets. In certain embodiments, the analyte is stained.

In certain embodiments, the spacers regulating the layer of uniform thickness have a filling factor of at least 1%, wherein the filling factor is the ratio of the spacer area in contact with the layer of uniform thickness to the total plate area in contact with the layer of uniform thickness. In certain embodiments, for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness. In certain embodiments, for a flexible plate, the thickness of the flexible plate times the Young's modulus of the flexible plate is in the range 60 to 750 GPa-um. In certain embodiments, for a flexible plate, the fourth power of the inter-spacer-distance (ISD) divided by the thickness of the flexible plate (h) and the Young's modulus (E) of the flexible plate, ISD$^4$/(hE), is equal to or less than 10$^6$ um$^3$/GPa.

In certain embodiments, one or both plates comprises a location marker, either on a surface of or inside the plate, that provide information of a location of the plate. In certain embodiments, one or both plates comprises a scale marker, either on a surface of or inside the plate, that provide information of a lateral dimension of a structure of the sample and/or the plate. In certain embodiments, one or both plates comprises an imaging marker, either on surface of or inside the plate, that assists an imaging of the sample. In certain embodiments, the spacers functions as a location marker, a scale marker, an imaging marker, or any combination of thereof.

In certain embodiments, the average thickness of the layer of uniform thickness is about equal to a minimum dimension of an analyte in the sample. In certain embodiments, the inter-spacer distance is in the range of 7 μm to 50 μm. In certain embodiments, the inter-spacer distance is in the range of 50 μm to 120 μm. In certain embodiments, the inter-spacer distance is in the range of 120 μm to 200 μm (micron). In certain embodiments, the inter-spacer distance is substantially periodic. In certain embodiments, the spacers are pillars with a cross-sectional shape selected from round, polygonal, circular, square, rectangular, oval, elliptical, or any combination of the same.

In certain embodiments, the spacers have a pillar shape and have a substantially flat top surface, wherein, for each spacer, the ratio of the lateral dimension of the spacer to its height is at least 1. In certain embodiments, each spacer has the ratio of the lateral dimension of the spacer to its height is at least 1. In certain embodiments, the minimum lateral dimension of spacer is less than or substantially equal to the minimum dimension of an analyte in the sample. In certain embodiments, the minimum lateral dimension of spacer is in the range of 0.5 um to 100 um. In certain embodiments, the minimum lateral dimension of spacer is in the range of 0.5 um to 10 um.

In certain embodiments, the sample is blood. In certain embodiments, the sample is whole blood without dilution by liquid. In certain embodiments, the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine. In certain embodiments, the sample is a biological sample, an environmental sample, a chemical sample, or clinical sample.

In certain embodiments, the spacers have a pillar shape, and the sidewall corners of the spacers have a round shape with a radius of curvature at least 1 μm. In certain embodiments, the spacers have a density of at least 100/mm$^2$. In certain embodiments, the spacers have a density of at least 1000/mm$^2$. In certain embodiments, at least one of the plates is transparent. In certain embodiments, at least one of the plates is made from a flexible polymer. In certain embodiments, for a pressure that compresses the plates, the spacers are not compressible and/or, independently, only one of the plates is flexible. In certain embodiments, the flexible plate has a thickness in the range of 10 um to 200 um. In certain embodiments, the variation is less than 30%. In certain embodiments, the variation is less than 10%. In certain embodiments, the variation is less than 5%.

In certain embodiments, the first and second plates are connected and are configured to be changed from the open configuration to the closed configuration by folding the plates. In certain embodiments, the first and second plates are connected by a hinge and are configured to be changed from the open configuration to the closed configuration by folding the plates along the hinge. In certain embodiments, the first and second plates are connected by a hinge that is a separate material to the plates, and are configured to be changed from the open configuration to the closed configuration by folding the plates along the hinge. In certain embodiments, the first and second plates are made in a single piece of material and are configured to be changed from the open configuration to the closed configuration by folding the plates. In certain embodiments, the layer of uniform thickness sample is uniform over a lateral area that is at least 1 mm$^2$.

In certain embodiments, the device is configured to analyze the sample in 60 seconds or less. In certain embodiments, at the closed configuration, the final sample thickness device is configured to analyze the sample in 60 seconds or less. In certain embodiments, at the closed configuration, the final sample thickness device is configured to analyze the sample in 10 seconds or less.

In certain embodiments, the dry binding site comprises a capture agent. In certain embodiments, the dry binding site comprises an antibody or nucleic acid. In certain embodiments, the releasable dry reagent is a labeled reagent. In certain embodiments, the releasable dry reagent is a fluorescently-labeled reagent. In certain embodiments, the releasable dry reagent is a fluorescently-labeled antibody. In certain embodiments, the releasable dry reagent is a cell stain. In certain embodiments, the releasable dry reagent is a cell lysing.

In certain embodiments, the detector is an optical detector that detects an optical signal. In certain embodiments, the detector is an electric detector that detect electrical signal. In certain embodiments, the spacing are fixed on a plate by directly embossing the plate or injection molding of the plate. In certain embodiments, the materials of the plate and the spacers are selected from polystyrene, PMMA, PC, COC, COP, or another plastic.

In certain embodiments of the present disclosure, a system for rapidly analyzing a sample using a mobile phone can comprise a device of any prior embodiment. In certain embodiments of the present disclosure, a system for rapidly analyzing a sample using a mobile phone can comprise a mobile communication device. In certain embodiments, the mobile communication device can comprise one or a plurality of cameras for the detecting and/or imaging the sample. In certain embodiments, the mobile communication device can comprise electronics, signal processors, hardware and software for receiving and/or processing the detected signal and/or the image of the sample and for remote communication. In certain embodiments, the mobile communication device can comprise a light source from either the mobile communication device or an external source. In same embodiments, the detector in the devices or methods of any prior embodiment is provided by the mobile communication device, and detects an analyte in the sample at the closed configuration.

In certain embodiments, one of the plates has a binding site that binds an analyte, wherein at least part of the uniform sample thickness layer is over the binding site, and is substantially less than the average lateral linear dimension of the binding site. In certain embodiments, any system of the present disclosure can comprise a housing configured to hold the sample and to be mounted to the mobile communication device. In certain embodiments, the housing comprises optics for facilitating the imaging and/or signal processing of the sample by the mobile communication device, and a mount configured to hold the optics on the mobile communication device. In certain embodiments, an element of the optics in the housing is movable relative to the housing. In certain embodiments, the mobile communication device is configured to communicate test results to a medical professional, a medical facility or an insurance company. In certain embodiments, the mobile communication device is further configured to communicate information on the test and the subject with the medical professional, medical facility or insurance company. In certain embodiments, the mobile communication device is further configured to communicate information of the test to a cloud network, and the cloud network process the information to refine the test results. In certain embodiments, the mobile communication device is further configured to communicate information of the test and the subject to a cloud network, the cloud network process the information to refine the test results, and the refined test results will send back the subject. In certain embodiments, the mobile communication device is configured to receive a prescription, diagnosis or a recommendation from a medical professional. In certain embodiments, the mobile communication device is configured with hardware and software to capture an image of the sample. In certain embodiments, the mobile communication device is configured with hardware and software to analyze a test location and a control location in in image. In certain embodiments, the mobile communication device is configured with hardware and software to compare a value obtained from analysis of the test location to a threshold value that characterizes the rapid diagnostic test.

In certain embodiments of the present disclosure, at least one of the plates comprises a storage site in which assay reagents are stored. In certain embodiments, at least one of the cameras reads a signal from the device. In certain embodiments, the mobile communication device communicates with the remote location via a wifi or cellular network. In certain embodiments, the mobile communication device is a mobile phone.

In certain embodiments of the present disclosure, a method for rapidly analyzing an analyte in a sample using a mobile phone can comprise depositing a sample on the device of any prior system embodiment. In certain embodiments of the present disclosure, a method for rapidly analyzing an analyte in a sample using a mobile phone can comprise assaying an analyte in the sample deposited on the device to generate a result. In certain embodiments of the present disclosure, a method for rapidly analyzing an analyte in a sample using a mobile phone can comprise communicating the result from the mobile communication device to a location remote from the mobile communication device.

In certain embodiments, the analyte comprises a molecule (e.g., a protein, peptides, DNA, RNA, nucleic acid, or other molecule), cells, tissues, viruses, and nanoparticles with different shapes. In certain embodiments, the analyte comprises white blood cell, red blood cell and platelets. In certain embodiments, the assaying comprises performing a white blood cells differential assay. In certain embodiments, a method of the present disclosure can comprise analyzing the results at the remote location to provide an analyzed result. In certain embodiments, a method of the present disclosure can comprise communicating the analyzed result from the remote location to the mobile communication device. In certain embodiments, the analysis is done by a medical professional at a remote location. In certain embodiments, the mobile communication device receives a prescription, diagnosis or a recommendation from a medical professional at a remote location.

In certain embodiments, the sample is a bodily fluid. In certain embodiments, the bodily fluid is blood, saliva or urine. In certain embodiments, the sample is whole blood without dilution by a liquid. In certain embodiments, the assaying step comprises detecting an analyte in the sample.

In certain embodiments, the analyte is a biomarker. In certain embodiments, the analyte is a protein, nucleic acid, cell, or metabolite. In certain embodiments, the method comprises counting the number of red blood cells. In certain embodiments, the method comprises counting the number of white blood cells. In certain embodiments, the method comprises staining the cells in the sample and counting the number of neutrophils, lymphocytes, monocytes, eosinophils and basophils. In certain embodiments, the assay done in step (b) is a binding assay or a biochemical assay.

In certain embodiments of the present disclosure, a method for analyzing a sample can comprise obtaining a device of any prior device embodiment. In certain embodiments of the present disclosure, a method for analyzing a sample can comprise depositing the sample onto one or both pates of the device. In certain embodiments of the present disclosure, a method for analyzing a sample can comprise placing the plates in a closed configuration and applying an external force over at least part of the plates. In certain embodiments of the present disclosure, a method for analyzing a sample can comprise analyzing the layer of uniform thickness while the plates are the closed configuration.

In certain embodiments, the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample. In certain embodiments, the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample. In certain embodiments, the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample. In certain embodiments, the analyte assay area is between a pair of electrodes. In certain embodiments, the assay area is defined by a patch of dried reagent. In certain embodiments, the assay area binds to and immobilizes the analyte. In certain embodiments, the assay area is defined by a patch of binding reagent that, upon contacting the sample, dissolves into the sample, diffuses in the sample, and binds to the analyte. In certain embodiments, the inter-spacer distance is in the range of 14 µm to 200 µm. In certain embodiments, the inter-spacer distance is in the range of 7 µm to 20 µm. In certain embodiments, the spacers are pillars with a cross-sectional shape selected from round, polygonal, circular, square, rectangular, oval, elliptical, or any combination of the same. In certain embodiments, the spacers have a pillar shape and have a substantially flat top surface, wherein, for each spacer, the ratio of the lateral dimension of the spacer to its height is at least 1. In certain embodiments, the spacers have a pillar shape, and the sidewall corners of the spacers have a round shape with a radius of curvature at least 1 µm. In certain embodiments, the spacers have a density of at least $1000/mm^2$. In certain embodiments, at least one of the plates is transparent. In certain embodiments, at least one of the plates is made from a flexible polymer. In certain embodiments, only one of the plates is flexible. In certain embodiments, the area-determination device is a camera. In certain embodiments, an area in the sample contact area of a plate, wherein the area is less than 1/100, 1/20, 1/10, 1/6, 1/5, 1/4, 1/3, 1/2, 2/3 of the sample contact area, or in a range between any of the two values. In certain embodiments, the area-determination device comprises a camera and an area in the sample contact area of a plate, wherein the area is in contact with the sample.

In certain embodiments, the deformable sample comprises a liquid sample. In certain embodiments, the imprecision force has a variation at least 30% of the total force that actually is applied. In certain embodiments, the imprecision force has a variation at least 20%, 30%, 40%, 50%, 60, 70%, 80%, 90% 100%, 150%, 200%, 300%, 500%, or in a range of any two values, of the total force that actually is applied. In certain embodiments, the spacers have a flat top. In certain embodiments, the device is further configured to have, after the pressing force is removed, a sample thickness that is substantially the same in thickness and uniformity as that when the force is applied. In certain embodiments, the imprecise force is provided by human hand. In certain embodiments, the inter spacer distance is substantially constant. In certain embodiments, the inter spacer distance is substantially periodic in the area of the uniform sample thickness area. In certain embodiments, the multiplication product of the filling factor and the Young's modulus of the spacer is 2 MPa or larger. In certain embodiments, the force is applied by hand directly or indirectly. In certain embodiments, the force applied is in the range of 1 N to 20 N. In certain embodiments, the force applied is in the range of 20 N to 200 N. In certain embodiments, the highly uniform layer has a thickness that varies by less than 15%, 10%, or 5% of an average thickness. In certain embodiments, the imprecise force is applied by pinching the device between a thumb and forefinger. In certain embodiments, the predetermined sample thickness is larger than the spacer height. In certain embodiments, the device holds itself in the closed configuration after the pressing force has been removed. In certain embodiments, the uniform thickness sample layer area is larger than that area upon which the pressing force is applied. In certain embodiments, the spacers do not significantly deform during application of the pressing force. In certain embodiments, the pressing force is not predetermined beforehand and is not measured. In certain embodiments, the fluidic sample is replaced by a deformable sample and the embodiments for making at least a part of the fluidic sample into a uniform thickness layer can make at least a part of the deformable sample into a uniform thickness layer. In certain embodiments, the inter spacer distance is periodic. In certain embodiments, the spacers have a flat top. In certain embodiments, the inter spacer distance is at least two times large than the size of the targeted analyte in the sample.

Manufacturing of Q-Card

In certain embodiments of the present disclosure, a Q-Card can comprise a first plate. In certain embodiments of the present disclosure, a Q-Card can comprise a second plate. In certain embodiments of the present disclosure, a Q-Card can comprise a hinge. In certain embodiments, the first plate, that is about 200 nm to 1500 nm thick, comprises, on its inner surface, (a) a sample contact area for contacting a sample, and (b) a sample overflow dam that surrounds the sample contact area is configured to present a sample flow outside of the dam. In certain embodiments, the second plate is 10 um to 250 um thick and comprises, on its inner surface, (a) a sample contact area for contacting a sample, and (b) spacers on the sample contact area. In certain embodiments, the hinge that connect the first and the second plates. In certain embodiments, the first and second plate are movable relative to each other around the axis of the hinge.

In certain embodiments of the present disclosure, an embodiment of the Q-Card can comprise a first plate. In certain embodiments of the present disclosure, an embodiment of the Q-Card can comprise a second plate. In certain embodiments of the present disclosure, an embodiment of the Q-Card can comprise a hinge. In certain embodiments, the first plate, that is about 200 nm to 1500 nm thick, comprises, on its inner surface, (a) a sample contact area for contacting a sample, (b) a sample overflow dam that surrounds the sample contact area is configured to present a sample flow outside of the dam, and (c) spacers on the sample contact area. In certain embodiments, the second plate, that is 10 um to 250 um thick, comprises, on its inner surface, a sample contact area for contacting a sample. In certain embodiments, the hinge connects the first and the second plates. In certain embodiments, the first and second plate are movable relative to each other around the axis of the hinge.

In certain embodiments of the present disclosure, an embodiment of the Q-Card can comprise a first plate. In certain embodiments of the present disclosure, an embodiment of the Q-Card can comprise a second plate. In certain embodiments of the present disclosure, an embodiment of the Q-Card can comprise a hinge. In certain embodiments, the first plate, that is about 200 nm to 1500 nm thick, comprises, on its inner surface, (a) a sample contact area for contacting a sample, and (b) spacers on the sample contact area. In certain embodiments, the second plate, that is 10 um to 250 um thick, comprises, on its inner surface, (a) a sample contact area for contacting a sample, and (b) a sample overflow darn that surrounds the sample contact area is configured to present a sample flow outside of the darn. In certain embodiments, the hinge connects the first and the second plates. In certain embodiments, the first and second plate are movable relative to each other around the axis of the hinge.

In certain embodiments of the present disclosure, an embodiment of the Q-Card can comprise a first plate. In certain embodiments of the present disclosure, an embodiment of the Q-Card can comprise a second plate. In certain embodiments of the present disclosure, an embodiment of the Q-Card can comprise a hinge. In certain embodiments, the first plate, that is about 200 nm to 1500 nm thick, comprises, on its inner surface, a sample contact area for contacting a sample. In certain embodiments, the second plate, that is 10 um to 250 um thick, comprises, on its inner surface, (a) a sample contact area for contacting a sample, (b) a sample overflow darn that surrounds the sample contact area is configured to present a sample flow outside of the darn, and (c) spacers on the sample contact area. In certain embodiments, the hinge connects the first and the second plates. In certain embodiments, the first and second plate are movable relative to each other around the axis of the hinge.

In certain embodiments of the present disclosure, a method for fabricating any Q-Card of the present disclosure can comprise injection molding of the first plate. In certain embodiments of the present disclosure, a method for fabricating any Q-Card of the present disclosure can comprise nanoimprinting or extrusion printing of the second plate.

In certain embodiments of the present disclosure, a method for fabricating any Q-Card of the present disclosure can comprise Laser cutting the first plate. In certain embodiments of the present disclosure, a method for fabricating any Q-Card of the present disclosure can comprise nanoimprinting or extrusion printing of the second plate.

In certain embodiments of the present disclosure, a method for fabricating any Q-Card of the present disclosure can comprise injection molding and laser cutting the first plate. In certain embodiments of the present disclosure, a method for fabricating any Q-Card of the present disclosure can comprise nanoimprinting or extrusion printing of the second plate.

In certain embodiments of the present disclosure, a method for fabricating any Q-Card of the present disclosure can comprise nanoimprinting or extrusion printing to fabricated both the first and the second plate.

In certain embodiments of the present disclosure, a method for fabricating any Q-Card of the present disclosure can comprise fabricating the first plate or the second plate, using injection molding, laser cutting the first plate, nanoimprinting, extrusion printing, or a combination of thereof.

In certain embodiments of the present disclosure, a method for fabricating any Q-Card of the present disclosure can comprise a step of attaching the hinge on the first and the second plates after the fabrication of the first and second plates.

Additional Examples and Definitions (1) Definitions

The terms used in describing the devices/apparatus, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(2) Sample

The devices/apparatus, systems, and methods herein disclosed can be applied to manipulation and detection of various types of samples. The samples are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter ($\mu$L, also "uL" herein) or less, 500 $\mu$L or less, 300 $\mu$L or less, 250 $\mu$L or less, 200 $\mu$L or less, 170 $\mu$L or less, 150 $\mu$L or less, 125 $\mu$L or less, 100 $\mu$L or less, 75 $\mu$L or less, 50 $\mu$L or less, 25 $\mu$L or less, 20 $\mu$L or less, 15 $\mu$L or less, 10 $\mu$L or less, 5 $\mu$L or less, 3 $\mu$L or less, 1 $\mu$L or less, 0.5 $\mu$L or less, 0.1 $\mu$L or less, 0.05 $\mu$L or less, 0.001 $\mu$L or less, 0.0005 $\mu$L or less, 0.0001 $\mu$L or less, 10 pL or less, 1 pL or less, or a range between any two of the values.

In some embodiments, the volume of the sample includes, but is not limited to, about 100 $\mu$L or less, 75 $\mu$L or less, 50 $\mu$L or less, 25 $\mu$L or less, 20 $\mu$L or less, 15 $\mu$L or less, 10 $\mu$L or less, 5 $\mu$L or less, 3 $\mu$L or less, 1 $\mu$L or less, 0.5 $\mu$L or less, 0.1 $\mu$L or less, 0.05 $\mu$L or less, 0.001 $\mu$L or less, 0.0005 $\mu$L or less, 0.0001 $\mu$L or less, 10 pL or less, 1 pL or less, or a range between any two of the values. In some embodiments, the volume of the sample includes, but is not limited to,about 10 $\mu$L or less, 5 $\mu$L or less, 3 $\mu$L or less, 1 $\mu$L or less, 0.5 $\mu$L or less, 0.1 $\mu$L or less, 0.05 $\mu$L or less, 0.001 $\mu$L or less, 0.0005 $\mu$L or less, 0.0001 $\mu$L or less, 10 pL or less, 1 pL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyimide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in U.S. Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a micro-controller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456,631, 62/456,522, 62/456,598, 62/456,603, and 62/456,628, which were filed on Feb. 8, 2017, U.S. Provisional Application No. 62/459,276, 62/456,904, 62/457,075, and 62/457,009, which were filed on Feb. 9, 2017, and U.S. Provisional Application No. 62/459,303, 62/459,337, and 62/459,598, which were filed on Feb. 15, 2017, and U.S. Provisional Application No. 62/460,083, 62/460,076, which were filed on Feb. 16, 2017, all of which applications are incorporated herein in their entireties for all purposes.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino--fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as Renilla reniformis, Renilla mulleri, or Ptilosarcus guernyi; "humanized" recombinant GFP (hrGFP); any of a variety of fluorescent and colored proteins from *Anthozoan* species; combinations thereof; and the like.

In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025.

In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipet, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

What is claimed is:

1. A device for analyzing an analyte in a liquid sample, comprising:
   (a) an attachment member configured to attach the device to an apparatus that comprises a light source and a camera;
   (b) a card slot configured to accommodate a sample card, wherein the sample card comprises two plates having a gap of 200 μm or less, that sandwich a liquid sample into a layer of uniform thickness, wherein when the sample card is inserted into the card slot, the sample is positioned under the view of the camera and the light source;
   (c) an optical filter configured to filter light from the light source to form a first beam with a specific wavelength range, wherein a part of the first beam illuminates on the edge of the sample card and travels inside the sample card to illuminate the sample;
   (d) a mirror configured to deflect a second part of the first beam to form a second beam that back-illuminates the sample in an oblique angle; and
   (e) an absorber configured to absorb a remaining part of the first beam that has a substantial divergence angle.

2. The device of claim 1, further comprising a lens, wherein the lens is positioned on a front-side of the sample and the configuration of the mirror is configured to make the oblique angle is larger of the second part of the first beam than a collecting angle of the lens.

3. The device of claim 1, further comprising a wavelength filter positioned between the sample and the camera to pass fluorescence emitted by the sample in response to the oblique illumination.

4. The device of claim 1, wherein the sample card is supported by a sample holder comprising a planar structure, and wherein the receptacle sample slot is configured to position the planar structure to extend partially into a path of illumination light from the light source to couple illumination light into the planar structure.

5. A method for analyzing an analyte in a liquid sample using the device of claim 1, comprising:
   (a) providing the device of claim 1;
   (b) obtaining the liquid sample;
   (c) compressing at least part of the sample into a layer of uniform thickness with a sample card,
   (c) inserting the sample card into the device of claim 1;
   (e) illuminating the sample with light from the light source
   wherein the sample card comprises:
       a first plate, a second plate, and spacers, wherein:
       (i) the plates are movable relative to each other into different configurations;
       (ii) one or both plates are flexible;
       (iii) each of the plates comprises an inner surface that has a sample contact area for contacting a blood sample;
       (iv) one or both of the plates comprise the spacers that are permanently fixed on the sample contact area of a respective plate;
       (vi) the spacers have:
           (a) a predetermined substantially uniform height that has a value selected in the range of 5 μm to 50 μm,
           (b) a shape of pillar with a substantially uniform cross-section and a flat top surface;
           (c) a ratio of the width to the height equal to or larger than one;
           (d) a predetermined, fixed, non-random, inter-spacer distance that is in the range of 10 μm to 200 μm (micron);
           (e) a filling factor of equal to 1% or larger, wherein the filling factor is the ratio of the spacer contact area (on the plate) to the total plate area; and
           (f) the filling factor multiplies the Young's modulus of the spacer is equal to 2 MPa or larger;
   wherein one of the configurations is an open configuration, in which: the two plates are partially or completely separated apart, the spacing between the plates is not regulated by the spacers, and the sample is deposited on one or both of the plates;
   wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

6. The method of claim 5, further comprising:
(f) capturing images of the sample in the layer of uniform thickness with the camera;
(g) analyzing the images to enumerate the analyte in the images; and
(h) calculating the concentration of the analyte in the sample based on the uniform thickness, a field of view of the camera, analyte number, and a predetermined correction factor;
wherein the field of view is the extent of the field in which the camera captures the images;
wherein the correction factor is determined by a miscount ratio, which is dependent on the field of view, the uniform thickness, and properties of the analyte.

7. The method of claim 5, wherein the liquid sample is a blood sample, the method further comprises:
(a) depositing the blood sample on one or both of the plates when the plates are configured in the open configuration,
(b) after (a), forcing the two plates into a closed configuration; and
(c) capturing images of sample in the layer of uniform thickness while the plates are the closed configuration; and
(d) analyzing the images to determine the concentration of white blood cells in the sample.

8. The method of claim 7, wherein the step of analyzing the images comprises
determining the respective number of white blood cells including neutrophils, lymphocytes, monocytes, eosinophils and basophils, through the counting of the cell number in the images and the analysis of the fluorescence color and shape for each white blood cell.

9. The method of claim 5, further comprising:
(a) analyzing the images to enumerate the analyte in the images,
(b) calculating the concentration of the analyte in the sample based on the uniform thickness, a field of view of the camera, the analyte enumeration, and a predetermined correction factor;
wherein the field of view is the area of sample of which the camera captures the images;
wherein the correction factor is determined by a miscount ratio, which is dependent on the field of view, the uniform thickness, and properties of the analyte.

10. The method of claim 6, wherein the correction factor is used to back calculate the WBC count to WBC concentration to compensate the WBC miss counting in the process.

11. The method of claim 6, wherein the correction factor depending on the size of the gap between the two plates of the sample holder is used to back calculate the WBC count to WBC concentration to compensate the WBC miss counting in the process.

12. The method of claim 6, wherein the correction factor is used to back calculate the WBC count to WBC concentration to compensate other imperfection effect as WBC distribution in the process.

13. The device of claim 1, wherein the sample card comprises:
a first plate, a second plate, and spacers, wherein:
(i) the plates are movable relative to each other into different configurations;
(ii) one or both plates are flexible;
(iii) each of the plates comprises an inner surface that has a sample contact area for contacting a blood sample;
(iv) one or both of the plates comprise the spacers that are permanently fixed on the sample contact area of a respective plate;
(vi) the spacers have:
(a) a predetermined substantially uniform height that has a value selected in the range of 5 μm to 50 μm,
(b) the fourth power of the inter-spacer-distance (ISD) divided by the thickness (h) and the Young's modulus (E) of the flexible plate (ISD$^4$/(hE)) is 5×10$^6$ μm$^3$/GPa, and
(c) the thickness of the flexible plate times the Young's modulus of the flexible plate is in the range 60 to 750 GPa-μm,
wherein one of the configurations is an open configuration, in which: the two plates are partially or completely separated apart, the spacing between the plates is not regulated by the spacers, and the sample is deposited on one or both of the plates;
another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

14. The method of claim 1, wherein the analyte is white blood cells (WBCs).

15. The device of claim 1, wherein the gap has a size in the range of 2 μm to 150 μm.

16. The device of claim 1, wherein the gap has a size in the range of 5 μm to 50 μm.

17. The device of claim 1, wherein the gap has a size in the range of 2 μm to 30 μm.

18. The device of claim 1, wherein the gap has a size in the range of 2 μm to 15 μm.

19. The device of claim 1, wherein a field of view for counting and differentiating WBCs is in the range of 1 mm$^2$ to 50 mm$^2$.

20. The device of claim 1, further comprising an anti-conglutination agent that is coated inside the sample card, the anti-conglutination agent comprises ethylenediaminetetraacetic acid (EDTA), EDTA disodium, K$_2$EDTA, or K$_3$EDTA, citrate, heparin, or any combinations thereof.

21. The device of claim 1, further comprising a fluorescence reagent for detecting the analyte.

22. The device of claim 1, further comprising a cell stain agent coated inside the sample card, the cell stain agent comprises Wright's stain (Eosin, methylene blue), Giemsa stain (Eosin, methylene blue, and Azure B), May-Grunwald stain, Leishman's stain ("Polychromed" methylene blue (i.e. demethylated into various azures) and eosin), Erythrosine B stain (Erythrosine B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (B021) dye, Ethidium Bromide, Brilliant Sulfaflavine and a Stilbene Disulfonic Acid derivative, Erythrosine B or trypan blue, Hoechst 33342, Trihydrochloride, Trihydrate, or DAPI (4', 6-Diamidino-2-Phenylindole, Dihydrochloride), YOYO or any combinations thereof.

23. The device of claim 1, further comprising a cell lysing agent coated inside the sample card, the cell lysing agent comprises ammonium chloride, sodium bicarbonate, ethylenediaminetetraacetic acid (EDTA), acetic acid, citric acid, or other acid and base, or any combinations thereof.

24. The device of claim 1, further comprising an agent coated on the sample card, wherein the agent comprises Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, Tween 20, Tween 40, Tween 60, Tween 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, Triton X-100, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, or phosphine oxide.

25. The device of claim 1, further comprising agent coated on the device, wherein the agent comprises Pluronic F-127, Cremophor EL, Pluronic F-68, Myrj 52, Brij 35, sodium oleate, sodium dodecyl sulfate, Tween 20, Tween 40, Tween 60, Tween 80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cisplatinum), nitrites, nitrofurantoin, penicillin, phenazopyridine (pyridium), rho immune globulin, ribavirin, sulfonamides, sulfones.

26. The device of claim 1, further comprising a release time control material icoated inside the device, wherein the release time control material comprises albumin, carbomers, carboxymethyl cellulose, carrageenan, chitosan, dextrin, polyethylene glycol, polyvinylpyrrolidone, or polyvinyl alcohol, or any combinations thereof.

27. The device of claim 1, further comprising a mobile device that comprises the camera and a light source.

28. The device of claim 1, further comprising a camera and a light source that provides the first beam.

29. The device of claim 1, further comprising an electronic hardware that comprises a machine learning model for analyzing the image and the analyte.

30. The device of claim 1, wherein the signal is a fluorescence signal.

31. The device of claim 1, wherein the device is configured to count neutrophils, eosinophils, basophils, lymphocytes, or monocytes.

32. The device of claim 13, wherein the spacers are periodic and have a period of less than 200 μm.

33. The device of claim 1, wherein the analyte is white blood cell, and wherein the device further comprises a hardware that contains a correction factor for correctly counting the white blood cell.

* * * * *